United States Patent
Mustaev et al.

(10) Patent No.: US 9,700,638 B2
(45) Date of Patent: Jul. 11, 2017

(54) NEAR INFRARED LABEL AND METHODS OF USE THEREOF

(71) Applicants: Rutgers, The State University of New Jersey, New Brunswick, NJ (US); New Jersey Institute of Technology, Newark, NJ (US)

(72) Inventors: Arkady Mustaev, New York, NY (US); David S. Perlin, New York, NY (US); Laura Wirpsza, Ocean City, NJ (US)

(73) Assignees: Rutgers, The State University of New Jersey, New Brunswick, NJ (US); New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 14/889,215

(22) PCT Filed: May 8, 2014

(86) PCT No.: PCT/US2014/037339
§ 371 (c)(1),
(2) Date: Nov. 5, 2015

(87) PCT Pub. No.: WO2014/182927
PCT Pub. Date: Nov. 13, 2014

(65) Prior Publication Data
US 2016/0106867 A1    Apr. 21, 2016

Related U.S. Application Data

(60) Provisional application No. 61/821,187, filed on May 8, 2013.

(51) Int. Cl.
| | | |
|---|---|---|
| A61K 49/00 | (2006.01) | |
| C07D 219/08 | (2006.01) | |
| C07D 401/12 | (2006.01) | |
| C07K 7/64 | (2006.01) | |
| C07D 405/14 | (2006.01) | |
| C07D 498/06 | (2006.01) | |

(52) U.S. Cl.
CPC ...... *A61K 49/0052* (2013.01); *A61K 49/0026* (2013.01); *C07D 219/08* (2013.01); *C07D 401/12* (2013.01); *C07D 405/14* (2013.01); *C07D 498/06* (2013.01); *C07K 7/64* (2013.01)

(58) Field of Classification Search
CPC ..... A61K 49/00; C07D 219/08; C07D 405/14
See application file for complete search history.

(56) References Cited

U.S. PATENT DOCUMENTS

| | | | |
|---|---|---|---|
| 4,892,858 A | | 1/1990 | Nakamine et al. |
| 2008/0299044 A1* | | 12/2008 | Texier-Nogues .. A61K 49/0032 424/9.6 |
| 2010/0256399 A1 | | 10/2010 | Smith et al. |
| 2011/0003343 A1 | | 1/2011 | Nikiforov et al. |

FOREIGN PATENT DOCUMENTS

| | | |
|---|---|---|
| JP | 2009091287 A | 4/2009 |
| WO | 03036299 A2 | 5/2003 |
| WO | 2008013997 A2 | 1/2008 |
| WO | 2012064733 A2 | 5/2012 |
| WO | 2013169932 A2 | 11/2013 |

OTHER PUBLICATIONS

Leevy et al., "Optical imaging of bacterial infection in living mice using a fluorescent near-infrared molecular probe," J Am. Chem. Soc. (2006); 128:16476-16477.
Lupetti et al., "Radiotracers for funal infection imaging," Med. Mycol. (2011); 49(Suppl 1): S62-S69.
Lupetti et al., "Technetium-99m labelled fluconazole and antimicrobial peptides for imaging of candida albicans and aspergillus fumigatus infections," European Journal of Nuclear Medicine and Molecular Imaging (May 1, 2002); 29(5):674-679.
Sabatelli et al., "In Vitro Activities of Posaconazole, Fluconazole, Itraconazole, Voriconazole, and Amphotericin B against a Large Collection of Clinically Important Molds and Yeasts," Antimicrobial Agents and Chemotherapy (Jun. 2006); 50(6):2009-2015.
Wareham et al., "Advances in bacterial specific imaging," Braz. Arch. Biol. Technol. (2005); 45:145-152.
Tung et al., "In Vivo Imaging of b-Galactosidase Activity Using Far Red Fluorescent Switch," Cancer Res (2004); 64:1579-1583.

\* cited by examiner

*Primary Examiner* — Michael G Hartley
*Assistant Examiner* — Jagadishwar Samala
(74) *Attorney, Agent, or Firm* — Fox Rothschild LLP

(57) ABSTRACT

The present invention provides compounds useful as novel near-infrared labels, compositions containing these compounds, and methods of using the near-infrared labels to identify targets in vitro, in situ and in vivo. The invention also provides small or large molecule conjugates between targeting agents and NIR labels, as well as methods and kits thereof, that can be used in diagnostics and treatment of diseases related to microbes in mammalian animals.

21 Claims, 13 Drawing Sheets

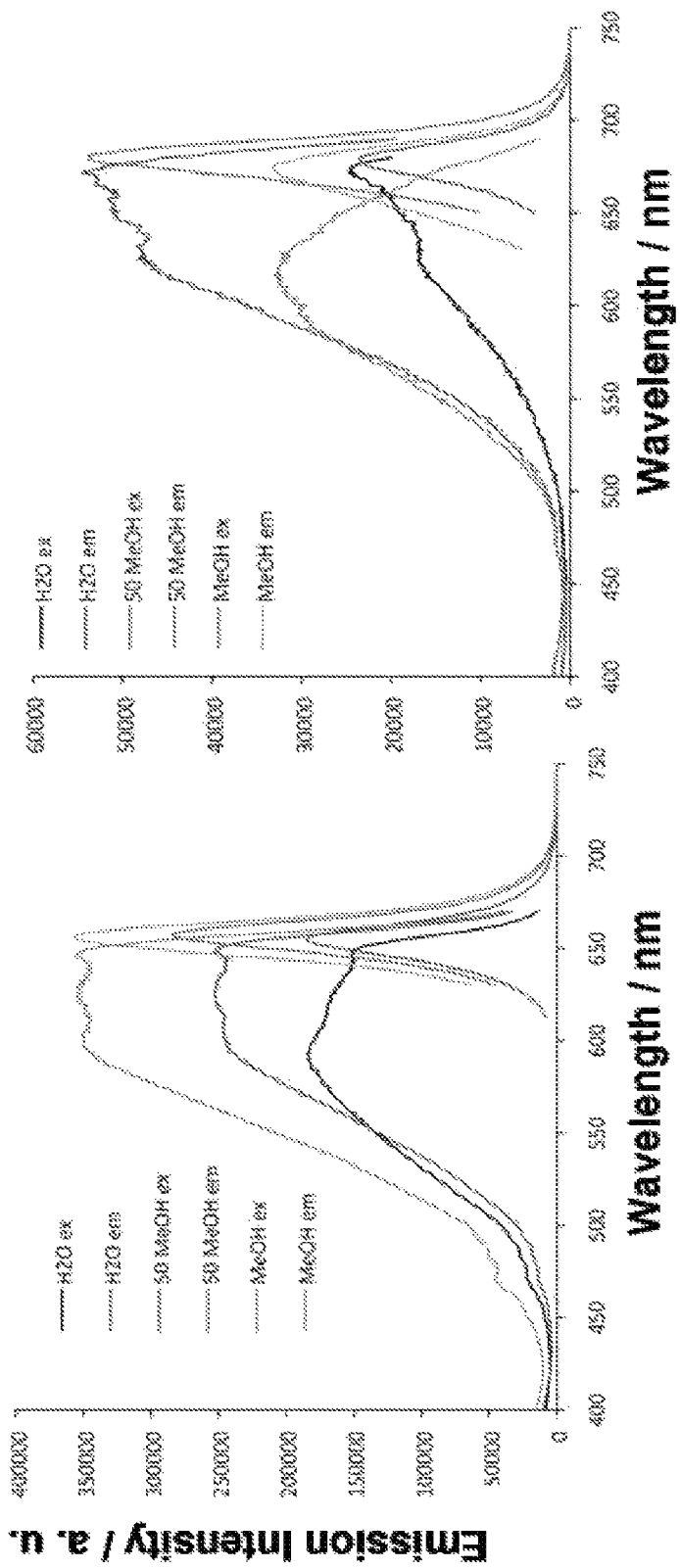
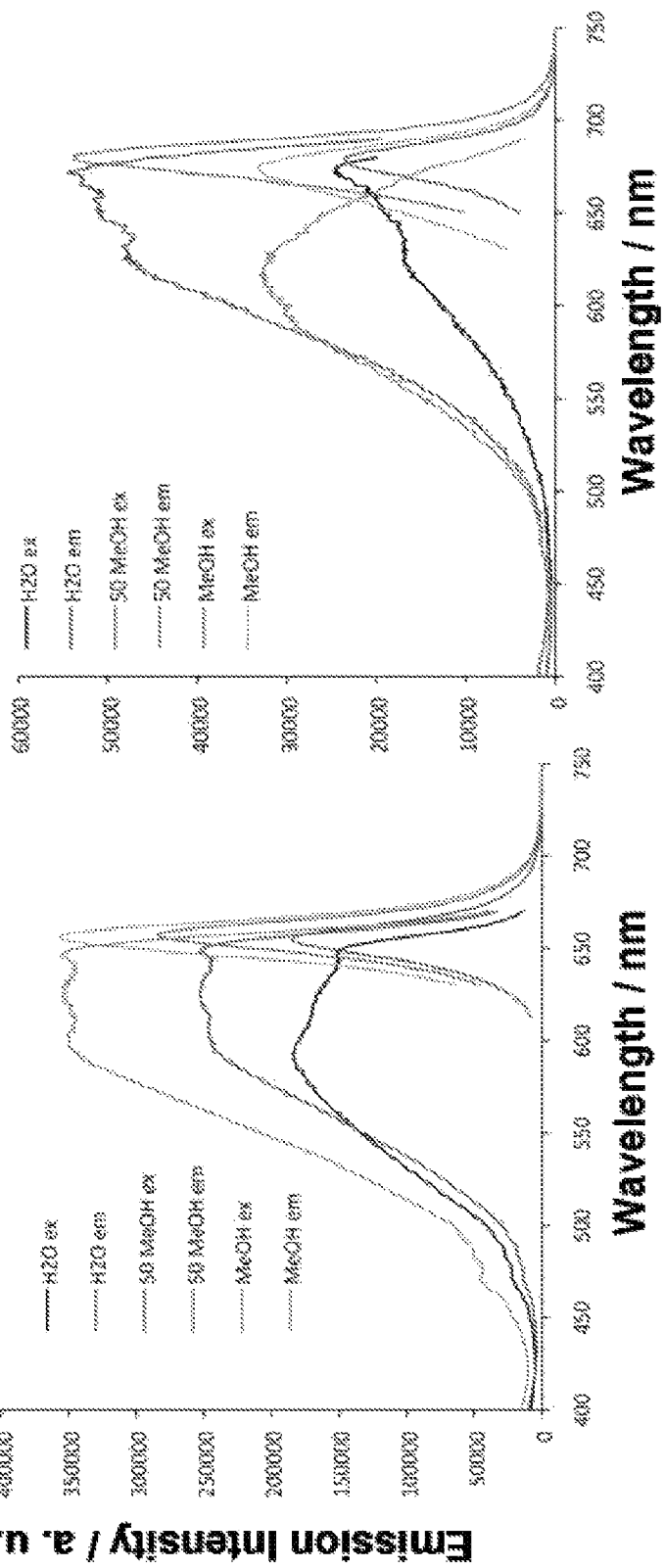
FIG. 5A
FIG. 5B

Antibacterial activity of Rif-DDAO compound

| Compound | MIC, µM |
|---|---|
| *S. aureus* | |
| Rif | 0.03 |
| Rif-DDAO | 0.008 |
| *B. subtilis* | |
| Rif | 0.1 |
| Rif-DDAO | 0.2 |

DDAO

Fluorescence

Light transmission

NEAR INFRARED LABEL AND METHODS OF USE THEREOF

CROSS REFERENCE TO RELATED APPLICATIONS

This application is a U.S. National Phase of International Application No. PCT/US2014/037339, filed May 8, 2014, which claims the benefit under 35 U.S.C. §119(e) of U.S. Provisional Application No. 61/821,187, filed on May 8, 2013, and the benefits of International Application No. PCT/US2013/040182, filed on May 8, 2013, which in turn claims priority under 35 U.S.C. §119(e) of U.S. Provisional Application No. 61/644,283, filed on May 8, 2012, all of which are incorporated herein by reference in their entirety.

STATEMENT REGARDING FEDERALLY SPONSORED RESEARCH

The invention described herein was supported in whole or in part by grants from the National Institutes of Health (NIH-GM-30717-21). The U.S. Government has certain rights in this invention.

FIELD OF THE INVENTION

The present invention relates to a novel near infrared label, compositions, and methods of using the label to identify targets in vitro, in situ and in vivo.

BACKGROUND OF THE INVENTION

Rapid detection of microbial pathogens in body tissues is a challenging task. Prompt diagnosis is crucial for successful therapeutic intervention in the case of infection by fast-growing pathogens or with immune-compromised individuals. The problem is aggravated due to increasing use of immunosuppressive agents in patients who receive transplants, implants, or more intensive anticancer therapies. Conventionally, detecting and monitoring infectious processes are achieved by use of various non-invasive imaging techniques, including conventional radiography, ultrasonography, computed tomography (CT), or magnetic resonance imaging (MRI). However, these techniques rely solely on morphological changes and, therefore, most abnormalities can only be detected at advanced stages of disease and diagnosis of early infections and differentiation between active and structural but indolent alterations following surgery or other interventions can be difficult. Also, morphological imaging methods cannot differentiate between sterile inflammation and infection and do not allow for timely monitoring to access the success of antimicrobial therapy at an early stage.

Fluorescence Molecular Tomography (FMT) is a powerful approach to image microbial infections in body tissues. It is based on using fluorescently labeled compounds (e.g. antibiotics) that recognize pathogen-specific targets, thereby rendering the pathogen cells fluorescent after binding to the targets. In FMT, imaging of fluorescent material (labeled microbial pathogens) in body is achieved through excitation by powerful light source and detection of the induced fluorescence. Moving the excitation source around a scanned object with simultaneous signal acquisition allows 3-D imaging of the area of interest. For these applications fluorescent group attached to the "address" molecule must have excitation and emission maxima in near-infrared (NIR) spectral range where body tissues are transparent.

The near infrared (NIR) range of the spectrum is a very promising area for fluorescence detection and imaging. Most fluorophores operate in the visible to ultraviolet range of the spectrum. In NIR much less background/noise is observed in both in vitro assays and tissue samples, thereby increasing detection sensitivity. Notably, body tissues have a transparency window in the region 650-800 nm with a maximal transparency at 680 nm, which enables non-invasive imaging of NIR dyes in the living body. Therefore, long wavelength emitting dyes are of a great demand for numerous biomedical applications such as imaging of pathogens inside the body. However, conventional NIR dyes tend to be large in size and possess groups with a stable electric charge (introduced to enhance a solubility of the compounds), and when conjugated to a targeting agent such as a drug, may affect the interaction of the modified drug with a target and cell permeability of the labeled drug derivatives. In particular, most current NIR fluorescent labels are bulky and contain a stable positive charge, which is likely to disable the "address" molecules by affecting their affinity to the targets. Therefore, new NIR labels, especially of small molecules, with desired properties are still in high demand.

SUMMARY OF THE INVENTION

The present invention provides much needed small-size near-infrared fluorophores suitable for attachment to biomolecules of interest. Due to the small size, these compounds preserve targeting properties of the "address" molecules when attached to them. The small-size near-infrared fluorophores have improved light-emission properties over the existing NIR labels, and their reactive derivatives are convenient for bioconjugation. These have been demonstrated by successful imaging of fungal pathogens with cultured cells and in body tissues using Fluorescent Molecular Tomography (FMT). Specifically, the invention relates to new derivatives of NIR fluorophore DDAO or analogs with improved spectral properties. The near-infrared labeling compounds include, but are not limited to, signaling molecular beacons-like non-nucleic acid-based diagnostic compounds, which are quenched, but become fluorescent upon binding to their targets.

In one aspect the present invention provides compounds of formula (I):

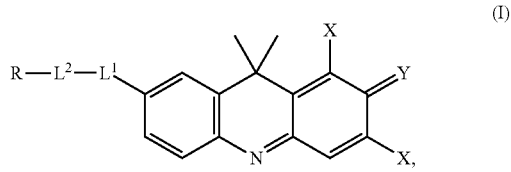

or a pharmaceutically acceptable salt or solvate thereof, wherein:
X at each occurrence is independently a halogen;
Y is O, S, or NR$^y$, wherein R$^y$ is hydrogen or $C_1$-$C_4$ alkyl;
L$^1$ is —NH— or —O—;
L$^2$ is a bond, a linear or branched alkylene, or a linear or branched heteroalkylene; and
R is hydrogen, a moiety of a biologically active molecule, or a functional group that can react with a biologically active molecule to form a covalent bond. Preferably, X, Y, L$^1$, L$^2$, and R are selected so that the compound is near-infrared fluorescent.

In one embodiment, the present invention provides a bioconjugate comprising a targeting agent, a moiety of a DDAO or 7-aminoDDAO derivative, and a linking group, wherein the targeting agent is an agent capable of detecting a target of interest in a biological sample or a subject.

The small size of the suggested NIR reporter group in combination with its fair brightness provides highly beneficial properties, which will make the corresponding detection probes useful in a variety of biomedical and research applications that rely on imaging of specific targets in body tissues. Competitive approaches (e.g. positron emission tomography, or PET) are based on using of radionuclides as labels for design of diagnostic probes. Short life time of radionuclides (from minutes to hours) and costs associated with their production, fast transportation and handling are major issues associated with their use. Also frequent use of radionuclides raises health concerns. Therefore, fluorescent labels in diagnostic microbe-targeting probes represent good alternative to radionuclides in this fast developing field.

In contrast, conventional near-infrared fluorophores are rarely suitable for the detection approach described above since they are bulky and in many cases possess a stable positive charge, which reduces the affinity of the probes to their targets and cellular uptake.

In another aspect the present invention provides a composition comprising a NIR label compound and bioconjugate as described, and a pharmaceutically acceptable carrier.

In another aspect the present invention provides methods of detecting a cell or a target in a cell of a subject or a biological sample of a subject, or detecting microbes in a subject or a biological sample of a subject, using a NIR label compound or bioconjugate as herein described, or a composition thereof.

In one embodiment, the present invention provides DDAO or 7-aminoDDAO compounds as NIR labels, in particular, derivatives of small-size NIR fluorophore DDAOs, such as 7-amino-DDAO derivatives, their compositions, methods of their preparation and synthesis, and methods of using them for detecting microbial targets in vitro, in situ, and in vivo.

These DDAO compounds include, but are not limited to, thiol- and amine-reactive NIR fluorescent labels as well as other click-reactive (such as azido- or alkynyl) derivatives.

In another embodiment, the present invention provides diagnostic compounds containing pathogen-targeting molecules labeled with the DDAO-derived fluorophores.

In another embodiment, the present invention provides methods of detecting and monitoring infectious processes in a subject by using these new NIR labels.

In another embodiment, the present invention provides a method of detecting bacterial pathogens in a subject, such as in body tissues, by using the new NIR label, in vitro or in vivo.

In another embodiment, the present invention provides methods of in vitro fluorescent detection of the bacterial pathogens comprising use of the diagnostic probes.

In another embodiment the present invention provides diagnostic probes comprising the DDAO NIR label and a pathogen-specific "address" molecule, and methods of using these diagnostic probes for detecting pathogens. These diagnostic probes and methods are useful for in vivo testing of the diagnostic probes with bacterial pathogens.

In another embodiment, the present invention provides methods of synthesizing DDAO conjugates with antibacterial drugs as diagnostic probes.

The details of these and other aspects or of the invention are set forth in the description below. Other features, objects, and advantages of the invention will be apparent from the description and the claims.

DETAILED DESCRIPTION OF THE INVENTION

Figure 1:
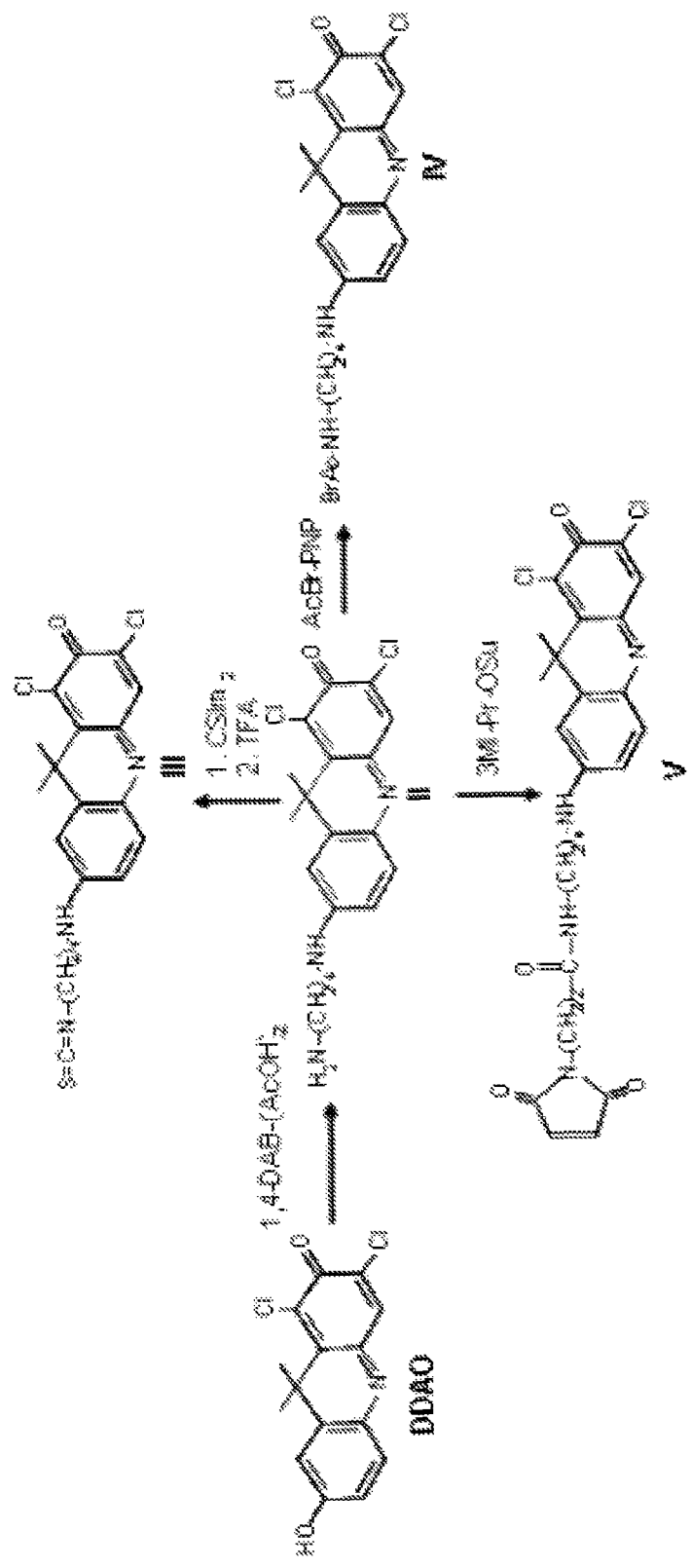
FIG. 1 depicts DDAO and the synthesis and light emission properties of 7-aminoDDAO and its cross-linkable derivatives.

The present invention relates to derivatives and analogs of the fluorophore, 7-hydroxy-9H-(1,3-dichloro-9,9-dimethyl-acridin-2-one), otherwise known as DDAO, methods of preparing and synthesizing DDAO derivatives, and the use of the DDAO derivatives as a label for detecting a target in vitro, in situ and in vivo.

In one aspect, the present invention provides a compound of formula (I):

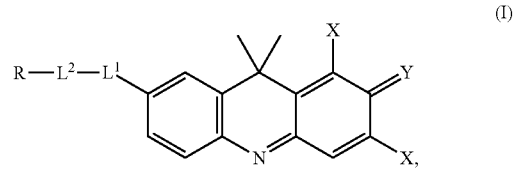

or a pharmaceutically acceptable salt or solvate thereof, wherein:
X at each occurrence is independently a halogen;
Y is O, S, or $NR^y$, wherein $R^y$ is hydrogen or $C_1$-$C_4$ alkyl;
$L^1$ is —NH— or —O—;
$L^2$ is a bond, a linear or branched alkylene, or a linear or branched heteroalkylene; and
R is hydrogen, a moiety of a biologically active molecule, or a functional group that can react with a biologically active molecule to form a covalent bond. Preferably, X, Y, $L^1$, $L^2$, and R are selected so that the compound is near-infrared fluorescent.

In one embodiment of this aspect, the alkylene has from 1 to 20 carbon atoms, and the heteroalkylene has from 1 to 15 carbon atoms and from 1 to 5 heteroatoms independently selected from O, N and S.

In another embodiment of this aspect, $L^2$ is —$(CH_2)_m$— or —$(CH_2CH_2O)_a$—$(CH_2)_b$—, wherein m is an integer selected from 1 to 10; a is 0 or an integer selected from 1 to 5, and b is an integer selected from 1 to 4.

In another embodiment of this aspect, R is —$NR^aR^b$, —NCS, —NCO, $C_1$-$C_6$ alkyl, amido, substituted or unsubstituted maleimido, or a click-reactive group (e.g., —$N_3$ or —C≡CH), or —C(O)—$R^1$;

wherein $R^a$ and $R^b$ are independently hydrogen or $C_1$-$C_4$ alkyl;

$R^1$ is —$N_3$ or —$OR^2$; and $R^2$ is $C_1$-$C_6$ alkyl or succinimido.

In another embodiment of this aspect, R is a moiety of a biologically active small or large molecule.

In another embodiment of this aspect, the biologically active small molecule is an antibacterial or antifungal agent.

In another embodiment of this aspect, the biologically active large molecule is an antibody, an antigen, a carbohydrate, a peptide, a nucleic acid, a lipid, or a synthetic or natural polymer.

In another embodiment of this aspect, $L^1$ is —NH—.

In another embodiment of this aspect, $L^1$ is —O—.

In another embodiment of this aspect, $L^1$ is —NH—; and $L^2$ is —$(CH_2)_m$—, wherein m is 2 to 6.

In another embodiment of this aspect, $L^1$ is —NH—; and $L^2$ is —$CH_2CH_2CH_2CH_2$—.

In another embodiment of this aspect, Y is O.

In another embodiment of this aspect, Y is S.

In another embodiment of this aspect, Y is $NR_y$, wherein $R_y$ is H or $C_1$-$C_4$ alkyl.

In another embodiment of this aspect, both X are Cl

In another embodiment of this aspect, both X are Cl; and Y is O.

In another embodiment of this aspect, the compound is selected from the group consisting of 7-amino-9H-(1,3-dichloro-9,9-dimethylacridin-2-one)(7-aminoDDAO), DDAO—NH—$(CH_2)_4$—$NH_2$, DDAO—NH—$(CH_2)_4$—NCS, DDAO—NH—$(CH_2)_4$—NH—$COCH_2X$ (wherein X is halogen), DDAO—NH—$(CH_2)_4$—NH-3-maleimide, a conjugate between Caspofungin and DDAO, a conjugate between Posaconazole and DDAO, and a conjugate between Rifampicin and DDAO.

In another embodiment of this aspect, the compound has a formula (II):

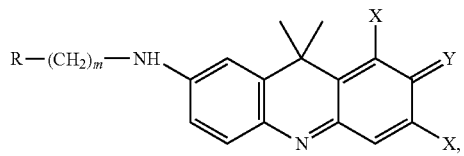

(II)

wherein R is selected from the group consisting of:

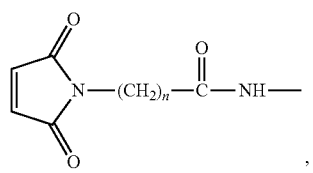

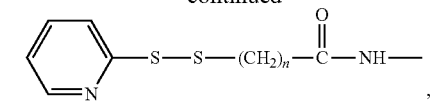

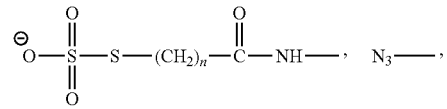

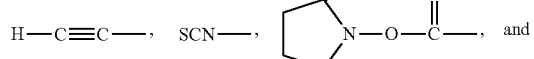

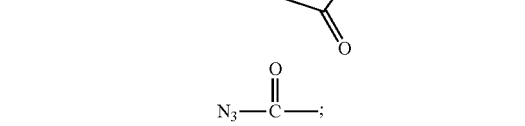

each X is independently a halogen;

Y is O, S, or $NR^y$, wherein $R^y$ is hydrogen or $C_1$-$C_4$ alkyl;

m is an integer selected from 1 to 10; and n at each occurrence is independently an integer selected from 1 to 10.

In another embodiment of this aspect, each X is independently F, Cl, or Br; m is 2 to 6; and n at each occurrence is 1 to 6.

In another embodiment of this aspect, $L^2$ is —$(CH_2)_m$—, wherein m is 2 to 6.

In another embodiment of this aspect, $L^2$ is —$CH_2CH_2CH_2CH_2$—.

In another embodiment of this aspect, Y is O.

In another embodiment of this aspect, Y is S.

In another embodiment of this aspect, Y is $NR^y$, wherein $R^y$ is H or $C_1$-$C_4$ alkyl.

In another embodiment of this aspect, both X are Cl

In another embodiment of this aspect, both X are Cl; and Y is O.

In another embodiment of this aspect, both X are Cl; Y is O; m is 2 to 4; and n at each occurrence is 2 to 4.

In other embodiments, the present invention encompasses any other combinations of the structural features described herein.

In another aspect, the present invention provides a composition comprising a compound according to any embodiments described herein, and a pharmaceutically acceptable carrier.

In another aspect the present invention provides a bioconjugate comprising a targeting agent, a moiety of a DDAO or 7-aminoDDAO derivative, and a linking group, wherein the targeting agent is an agent capable of detecting a target of interest in a biological sample or a subject.

In one embodiment of this aspect, the targeting agent is an antibody, an antigen, a carbohydrate, a peptide, a nucleic acid, a lipid, a synthetic or natural polymer, a small molecule, or a combination thereof.

In another embodiment of this aspect, the target is a glycoprotein, lipopolysaccharide, lipopeptide, a component of a cell wall, a receptor, or a combination thereof.

In another embodiment of this aspect, the linking group is selected from peptide linkers, self-immolative linkers, acid sensitive linkers, multifunctional organic linking agents, bifunctional inorganic crosslinking agents, polymers, and combinations thereof.

In another embodiment of this aspect, the linking group is stable, biodegradable, and/or cleavable under physiological conditions.

In another embodiment of this aspect, the targeting agent is a small molecule and/or a drug.

In another embodiment of this aspect, the small molecule is an antibacterial, or antifungal agent.

In another aspect the present invention provides a composition comprising a bioconjugate according to any embodiments described herein, and a pharmaceutically acceptable carrier.

In another aspect the present invention provides a method of detecting a cell or a target in a cell of a subject, comprising administering to the subject a compound and/or a bioconjugate according to any embodiment described herein, and detecting NIR fluorescence of the compound or the bioconjugate.

In another embodiment of this aspect, the compound is a conjugate between a DDAO derivative and a targeting agent.

In another embodiment of this aspect, said detecting comprises use of an imaging device.

In another aspect the present invention provides a cell or a target in a cell of a biological sample, comprising contacting the biological sample with a compound according to any embodiment of the present invention, and detecting NIR fluorescence of the compound.

In another embodiment of this aspect, the compound is a conjugate between a DDAO derivative and a targeting agent.

In another aspect the present invention provides a method of detecting a microbe in a subject, comprising administering to said subject a compound and/or a bioconjugate according to any embodiment described herein, and detecting NIR fluorescence of the compound or the bioconjugate.

In one embodiment of this aspect, the compound or bioconjugate comprises a DDAO or 7-aminoDDAO moiety.

In another embodiment of this aspect, the subject is administered a pretreatment antimicrobial drug prior to the administration of said compound or bioconjugate.

In another embodiment of this aspect, said detecting comprises using an imaging device.

In another embodiment of this aspect, the imaging device is selected from the group consisting of an x-ray imaging device, an infrared imaging device, fluorescent imaging device, nuclear magnetic resonance imaging device, magnetic resonance spectroscopy device, and a positron emission tomography device.

In another aspect the present invention provides a kit for detecting a microbe in a biological sample or a subject comprising a compound or bioconjugate according to any one of embodiments described herein, and instructions for use.

DDAO Derivatives

In one embodiment the present invention provides DDAO derivatives that contain an amine or amino group at position 7 instead of a hydroxyl group. In a preferred embodiment the hydroxyl group is replaced with a moiety having the following formula NH—$(CH_2)_m$-A, wherein m=1-10 and A=—$NH_2$, —NCS, an alkyl group, haloacetamido, acylmaleimido, or click-reactive (e.g., azido or alkynyl group). $(CH_2)_m$ may also be replaced with another spacer or polymer such as polyethylene glycol or other polymers that have the same properties and length. A DDAO fluorophore that contains an amino group at position 7 is herein referred to as 7-aminoDDAO. 7-aminoDDAO derivative (compound II of FIG. 1) has many superior properties compared to other NIR fluorophores: (1) it is small in size (FW=294); (2) has long-wavelength emission (640-700 nm); (3) exhibits fair brightness; (4) is pH-independent; (5) has emission maximum 680 nm, at which the body tissues are the most transparent; and (6) can be easily attached to a molecule of interest either directly, or through its simple conversion to amine-, thiol-, or click-reactive forms. In contrast, DDAO itself is pH-dependent due to the presence of a phenol hydroxyl group, and has emission maximum at 660 nm, a molar absorbance of 48,000 (vs. 53,000 for 7-aminoDDAO), and a brightness of 3,600 (vs. 6,000 for 7-aminoDDAO).

The synthetic protocol for compound II includes simple one-step conversion, followed by fast, non-chromatography purification. In a further embodiment, the present invention provides DDAO derivatives that are 1.4-2.3 fold brighter then original DDAO. DDAO derivatives may be used for covalent labeling of a biomolecule of interest, such as a targeting agent. The synthetic intermediate 7-(4-aminobutyl)aminoDDAO can be easily converted to other reactive forms (e.g. thiol-, or click-reactive), which are useful for bioconjugation, using methods known in the art. The structures of some of these reactive compounds (III-V) are shown in FIG. 1.

In a further embodiment, the present invention provides compositions comprising DDAO derivatives, which may be directly conjugated or covalently attached to a targeting agent, or attached to a targeting agent using a linker. The targeting agent conjugated to a DDAO derivative may be used to detect a target in a biological sample, such as a target in a cell or in a subject. The targeting agent may be any agent capable of detecting a target of interest in a biological sample, including for example an antibody, an antigen, a carbohydrate, a peptide, a nucleic acid, a synthetic or natural polymer, a small molecule or a combination thereof. The target may be a peptide, nucleic acid, antibody, antigen, carbohydrate, peptide, lipid, or a combination thereof, such as a glycoprotein, lipopolysaccharide, lipopeptide, or a component of a cell wall or a receptor.

As used herein, the phrase "near-infrared fluorescent" or the like refers to the property of a molecule that emits in the range of about 600 to 800 nm, with an emission maximum in the range of about 650 to 750 nm, preferably emitting in the range of 650-750 nm, with an emission maximum about 660 to 700 nm, and more preferably having an emission maximum around 680 nm.

The term "antibody" refers to an immunoglobulin or antigen-binding fragment thereof, and encompasses any such polypeptide comprising an antigen-binding fragment of an antibody. The term includes but is not limited to polyclonal, monoclonal, monospecific, polyspecific, humanized, human, single-chain, single-domain, chimeric, synthetic, recombinant, hybrid, mutated, grafted, and in vitro generated antibodies. The term "antibody" also includes antigen-binding fragments of an antibody. Examples of antigen-binding fragments include, but are not limited to, Fab fragments (consisting of the VL, VH, CL and CH1 domains); Fd fragments (consisting of the VH and CH1 domains); Fv fragments (referring to a dimer of one heavy and one light chain variable domain in tight, non-covalent association); dAb fragments (consisting of a VH domain); single domain fragments (VH domain, VL domain, VHH domain, or VNAR domain); isolated CDR regions; (Fab')2 fragments, bivalent fragments (comprising two Fab fragments linked by a disulphide bridge at the hinge region); scFv (referring to a fusion of the VL and VH domains, linked together with a short linker), and other antibody fragments that retain antigen-binding function.

The terms "polypeptide", "peptide", "protein", and "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, "nucleic acid" or "oligonucleotide" or "polynucleotide" or "nucleotide sequence" means at least two nucleotides covalently linked together. Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

As used herein, the term "linker" or "linking group" refers to a chemical moiety that connects a molecule to another molecule, covalently links separate parts of a molecule or separate molecules. The linker provides spacing between the two molecules or moieties such that they are able to function in their intended manner. Examples of linking groups include peptide linkers, enzyme sensitive peptide linkers/linkers, self-immolative linkers, acid sensitive linkers, multifunctional organic linking agents, bifunctional inorganic crosslinking agents, polymers and other linkers known in the art. The linker may be stable or degradable/cleavable. Various linkers are known in the art.

As used here, the term "biologically active compound" or the like refers to a compound having a physiological or biological effect on animals or humans, including but not limited to naturally occurring, semi-synthetic, or synthetic small or large molecule drugs, as well as cellular metabolites and signaling molecules (e.g. hormones, pheromones, etc.). Biologically active compounds capable of coupling to a DDAO or 7-aminoDDAO derivatives or analogs possess at least one functional group (e.g., hydroxyl, amine, or carboxyl, etc.) that can react with a DDAO or 7-aminoDDAO derivative or analog to form a conjugate. The method of forming such conjugate should be apparent to a person skilled in the art based on the present disclosure. Preferred biologically active compounds for the present invention include those that can serve as targeting agents for certain desired purposes, for example, binding to a specific target.

A biologically active compound can be a small molecule therapeutic agent, such as an antibacterial or antifungal agent. Examples of antibacterial agents include, but are not limited to, aminoglycosides, amikacin, gentamicin, kanamycin, neomycin, netilmicin, tobramycin, paromomycin, spectinomycin, ansamycins, geldanamycin, herbimycin, rifaximin, streptomycin, carbacephem, loracarbef, carbapenems, ertapenem, doripenem, imipenem, cilastatin, meropenem, cephalosporins, cefadroxil, cefazolin, cefalotin, cefalothin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftaroline fosamil, ceftobiprole, glycopeptides, teicoplanin, vancomycin, telavancin, lincosamides, clindamycin, lincomycin, lipopeptide, daptomycin, macrolides, azithromycin, clarithromycin, dirithromycin, erythromycin, roxithromycin, troleandomycin, telithromycin, spiramycin, monobactams, aztreonam, nitrofurans, furazolidone, nitrofurantoin, oxazolidonones, linezolid, posizolid, radezolid, torezolid, penicillins, amoxicillin, ampicillin, azlocillin, carbenicillin, cloxacillin, dicloxacillin, flucloxacillin, mezlocillin, methicillin, nafcillin, oxacillin, piperacillin, temocillin, ticarcillin, bacitracin, colistin, polymyxin b, quinolones, fluoroquinolone, ciprofloxacin, enoxacin, gatifloxacin, gemifloxacin, levofloxacin, lomefloxacin, moxifloxacin, nalidixic acid, norfloxacin, ofloxacin, trovafloxacin, grepafloxacin, sparfloxacin, temafloxacin, sulfonamides, mafenide, sulfacetamide, sulfadiazine, silver sulfadiazine, sulfadimethoxine, sulfamethizole, sulfamethoxazole, sulfasalazine, sulfisoxazole, trimethoprim-sulfamethoxazole (co-trimoxazole) (tmp-smx), tetracyclines, demeclocycline, doxycycline, minocycline, oxytetracycline, clofazimine, dapsone, capreomycin, cycloserine, ethambutol, ethionamide, isoniazid, pyrazinamide, rifampicin, rifabutin, rifapentine, streptomycin, arsphenamine, chloramphenicol, fosfomycin, fusidic acid, metronidazole, mupirocin, platensimycin, quinupristin/dalfopristin, thiamphenicol, tigecycline, tinidazole, and trimethoprim.

Examples of antifungal agents include, but are not limited to, natamycin, rimocidin, filipin, nystatin, amphotericin B, candicin, miconazole, ketoconazole, clotrimazole, econazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, abafungin, terbinafine, amorolfine, naftifine, butenafine, anidulafungin, caspofungin, and micafungin.

Biologically active compounds also include large molecules, including but not limited to antibodies, an antigens, carbohydrates, proteins, polypeptides, nucleic acids, lipids, or synthetic or natural polymers.

As used herein, the term "targeting agent" or the like refers to a moiety that recognizes, binds or adheres to a target molecule located, for example, in a cell, tissue, organism, or subset thereof. A targeting agent and its target molecule represent a binding pair of molecules, which interact with each other through any of a variety of molecular forces such as ionic, covalent, metal ions-mediated coordination, hydrophobic, van der Waals, and hydrogen bonding, so that the pair have the property of binding specifically to each other as known in the art.

The terms "group," "functional group," "moiety," "molecular moiety," or the like are somewhat synonymous in the chemical arts and are used to refer to distinct, definable portions or units of a molecule, and to units that perform some function or activity and are reactive with other molecules or portions of molecules. As used herein, a "moiety" or "molecular moiety" of a biologically active compound refers to a major portion of the biologically active compound that is expected to retain the function of the parent molecule when it forms a conjugate with a DDAO or 7-aminoDDAO derivative or analog. Examples of reactive functional groups that are suitable for the present invention include, but are not limited to, hydroxyl, amino, thiol, disulfide, carboxyl, carboxylate ester, sulfonic acid, sulfonate ester, amido, alkynyl, alkenyl, azido, cyanate, isocyanate, thiocyanate, isothiocyante, nitrile, isonitrile, or the like.

As used herein, the term "alkylene" refers to a straight or branched aliphatic divalent hydrocarbon group, in one embodiment having from 1 to about 20 carbon atoms. In a further embodiment alkylene includes lower alkylene (typically $C_1$-$C_6$, and in some embodiments, preferably $C_1$-$C_4$).

As used herein, the term "heteroalkylene" refers an alkylene group wherein one or more carbon atoms in its backbone are replaced by heteroatoms, such as O, N, and S, which includes, e.g., an oligomeric ethylene glycol moiety. Both alkylene and heteroalkylene groups can be substituted by one or more substituents, such as hydroxyl, halogen, amino, nitro, lower alkyl, $C_1$-$C_4$alkoxy, or the like.

As used herein, the term "halo" or "halogen" refers to F, Cl, Br, or I.

As used herein, the term "click-reactive group" or the like refers to a functional group that can participate in certain highly specific reactions (called bioorthogonal, since the reactants link only to each other, but not to any other biomolecules, or media components) to link two molecular moieties together, which has been called "click chemistry." Examples of "click-reactive groups include, but are not limited to, azido and terminal alkynyl group, which can be linked to each other in reactions such as: i) copper-free (with strained alkyne), or copper-catalyzed Huisgen cycloaddition or the 1,3-dipolar cycloaddition between an azide and a terminal alkyne to form a 1,2,4-triazole, ii) a Diels-Alder reaction, which is a cycloaddition reaction between a diene and a dienophile, and/or iii) nucleophilic substitution reactions in which one of the reactive species is an epoxy or aziridine compound with significant ring strain. See, e.g., US 20050222427 (Sharpless, et al.). Any clickable compound capable of linking a DDAO derivative with a biologically active compound is regarded as being within the scope of the present invention.

In certain embodiments the targeting agent may be a small molecule and/or a drug. Examples of small molecules include antifungal agents such as echinofungins and triazoles.

The DDAO derivatives of the invention may be formulated as a pharmaceutical composition, and may be administered to a mammalian host, such as a human patient, in a variety of forms adapted to the chosen route of administration, i.e., orally or parenterally, by intravenous, intramuscular, topical, subcutaneous, or other routes. Thus, the pharmaceutical composition of the invention may be systemically administered, e.g., orally, in combination with a pharmaceutically acceptable vehicle such as an inert diluent. They may be incorporated directly with the food of the patient's diet. For oral therapeutic administration, the compositions of the invention may be used in the form of elixirs, syrups, and the like.

Any material used in preparing any unit dosage form should be pharmaceutically acceptable and substantially non-toxic in the amounts employed. To administer the pharmaceutical composition to a patient, it is preferable to formulate the molecules in a composition comprising one or more pharmaceutically acceptable carriers. The phrase "pharmaceutically acceptable" refers to molecular entities and compositions that do not produce allergic, or other adverse reactions when administered using routes well-known in the art. "Pharmaceutically acceptable carriers" include any and all clinically useful solvents, dispersion media, coatings, antibacterial and antifungal agents, isotonic and absorption delaying agents and the like.

The pharmaceutical composition of the present invention can be administered to a subject by any of a number of means known in the art. A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model. Typically, the terms "subject" and "patient" are used interchangeably herein in reference to a human subject.

The pharmaceutical composition of the invention may also be administered intravenously or intra-peritoneally by infusion or injection, among many other routes. Solutions may be prepared, for example, in water. However, other solvents may also be employed. Under ordinary conditions of storage and use, these preparations may contain a preservative to prevent the growth of microorganisms, and other formulation ingredients as is known in the art.

The pharmaceutical dosage forms suitable for injection or infusion should be preferably sterile, fluid and stable under the conditions of manufacture and storage. The prevention of the action of microorganisms may be brought about by various antibacterial and antifungal agents, for example, parabens, chlorobutanol, phenol, sorbic acid, thimerosal, and the like. Others are also suitable. In many cases, it may be preferable to include isotonic agents, for example, sugars, buffers or sodium chloride.

Sterile injectable solutions may be prepared by incorporating the pharmaceutical composition of the invention in the required amount into an appropriate solvent or medium with various other ingredients, e.g., those enumerated above, as needed, which may be followed by sterilization. The above-described pharmaceutical composition containing the nanoparticles can be used to treat cancer.

In a further embodiment, the present invention provides a method to detect a target in a cell of interest comprising contacting a cell with a pharmaceutical composition comprising a DDAO derivative attached to a targeting agent.

In a further embodiment, the present invention provides a method to detect a cell comprising contacting a cell in a biological sample with a pharmaceutical composition comprising a DDAO derivative attached to a targeting agent. One with ordinary skill in the art will adapt the proper modality to detect pharmaceutical compositions as described. Such modalities include Fourier transform infrared spectroscopy.

In a further embodiment, the present invention provides a method to detect a target in a subject comprising administering to a subject a pharmaceutical composition comprising a DDAO derivative attached to a targeting agent. One with ordinary skill in the art will adapt the proper modality to detect pharmaceutical compositions as described. Such modalities include Fourier transform infrared spectroscopy.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference in their entireties.

The following non-limiting examples set forth herein below illustrate certain aspects of the invention.

EXAMPLES

Synthesis of DDAO-Based Fluorescent Derivatives

Example 1

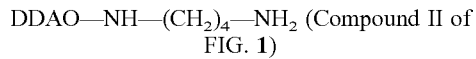

10 mg DDAO (7-hydroxy-9H (1,3-dichloro-9,9-dimethyl acridin-2-one)) (33 µmol) was dissolved in 100 µl 1M diaminobutane diacetate in 80% aqueous DMSO. After 10 h incubation at 95° C. TLC analysis in acetonitrile-water (14:1) developing system detected intense-blue colored product migrating lower (Rf=0.45) than the original product (Rf=0.9). The reaction mixture was supplemented with 2 ml of water and extracted with ethylacetate (3×5 ml). The pH of the water layer was adjusted to 11-11.5 by 10 M KOH followed by extraction with ethylacetate (2×5 ml). The organic layer was collected and evaporated to dryness under reduced pressure affording 4 mg of compound I. UV $\lambda_{max}$=673 nm ($\epsilon$=53,000 M$^{-1}$ cm$^{-1}$). MS: DDAO—NH—(CH$_2$)$_4$—NH$_2$ (+1) 378.0887 (found); 378.288 (calculated).

Example 2

DDAO—NH—(CH$_2$)$_4$—NCS (Compound III of FIG. 1)

15 mM Solution of compound I in 150 µl of DMSO was supplemented with 2 molar equivalent of 1,1-thiocarbonylimidazole dissolved in 0.2 ml of chloroform. After 30 min incubation at room temperature the mixture was supplemented with 1 ml of trifluoroacetic acid and incubation continued at 40° C. for another 45 min. TLC analysis in hexane-acetone (2:1) developing system showed complete conversion of the original compound (Rf=0) to reaction product (Rf=0.5). The reaction mixture was diluted by water and the product extracted in chloroform. The solvent was removed by evaporation in vacuo, and the residue dried by co-evaporation with acetonitrile. The product was purified by preparative TLC in hexane-acetone (2:1) developing system. Yield: 4 µmol. UV: λmax=673 nm ($\epsilon$=53 000 M-1 cm-1). MS: DDAO—NH—(CH$_2$)$_4$—NCS (+1) 420.0453 (found); 420.352 (calculated).

Example 3

DDAO—NH—(CH$_2$)$_4$—NH—AcBr (Compound IV of FIG. 1)

Equivalent amounts of p-nitrophenyl bromoacetate and compound I in DMF (0.46 µmol) were mixed and left for 5 minutes at room temperature. The sky blue product with $R_f$=0.58 was purified by TLC in ethyl acetate developing system. The product was eluted by 100% McOH and evaporated to final concentration 2.16 mM. Yield: 0.22 µmol (~48%). UV: $\lambda_{max}$=673 nm ($\epsilon$=53,000 M$^{-1}$ cm$^{-1}$). MS: DDAO—NH—(CH$_2$)$_4$—NH—AcBr 499.045 (found) 499.213 (calculated). DDAO—NH—(CH$_2$)$_4$—NH—AcBr (+H) 500.044 (found); 500.221 (calculated).

Example 4

DDAO—NH—CH$_2$)$_4$—NH-3MI (Compound V of FIG. 1)

Equivalent amounts of compound I (0.46 µmol) and N-succinimidyl-3-maleimidopropionate (MIpr-OSuc) were mixed in 122 µL DMF and kept at 0° C. for 15 minutes. TLC analysis in a 100% ethyl acetate developing system revealed two products, blue ($R_f$=0.5) and one purple. The Blue product was purified by preparative TLC in ethyl acetate developing system and eluted with MeOH. The eluate was concentrated by evaporation under reduced pressure affording 0.1 ml of 1.37 mM solution. Yield: 0.14 µmol (~30%). UV: $\lambda_{max}$=673 nm ($\epsilon$=53,000 M$^{-1}$ cm$^{-1}$). MS: DDAO—NH—(CH$_2$)$_4$—NH-3MI 529.154 (found); 529.40 (calculated). DDAO—NH—(CH$_2$)$_4$—NH-3MI (+H) 530.167 (found); 530.40 (calculated).

Example 5

Figure 2:
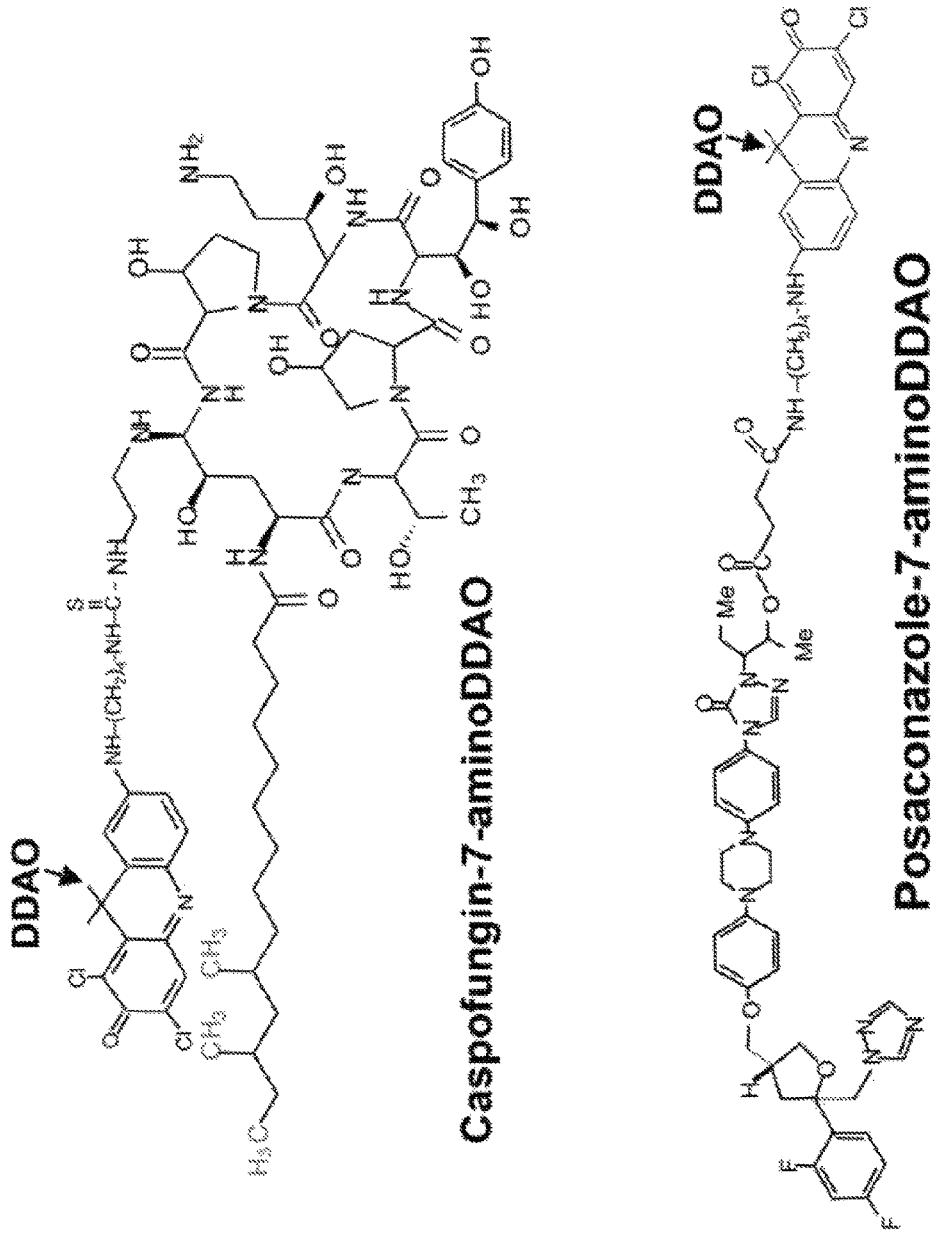
FIG. 2 depicts antifungal drugs labeled with 7-aminoDDAO.

Caspofungin—DDAO Derivative (FIG. 2, Top)

Caspofungin (2.6 mg, 2 µmol) was dissolved in the solution of 230 µl of 5 mM DDAO—NH—(CH2)4-NCS in DMF and 0.5 µl of triethylamine (TEA) was added followed by incubation at 60° C. for 90 min. TLC in acetonitrile-water (5:1) developing system detected a blue-colored reaction product with Rf=0.65. Rfs for caspofungin and DDAO—NH—(CH2) 4-NCS were 0.48 and 1.0 respectively. The product was purified by preparative TLC in acetonitrile-water (7:1) developing system, eluted by 50% aqueous methanol and the solution evaporated under reduced pressure to final concentration 0.33 mM. Yield: 50%. UV: $\lambda_{max}$=673 nm ($\epsilon$=53 000 M$^{-1}$ cm$^{-1}$). DDAO—NH—(CH$_2$)$_4$—NCS-Caspofungin (+H) 1515.7242 (found); 1515.673 (calculated).

Synthesis of Posaconazole-DDAO Derivatives (FIG. 2, Bottom)

Example 6

Figure 3:
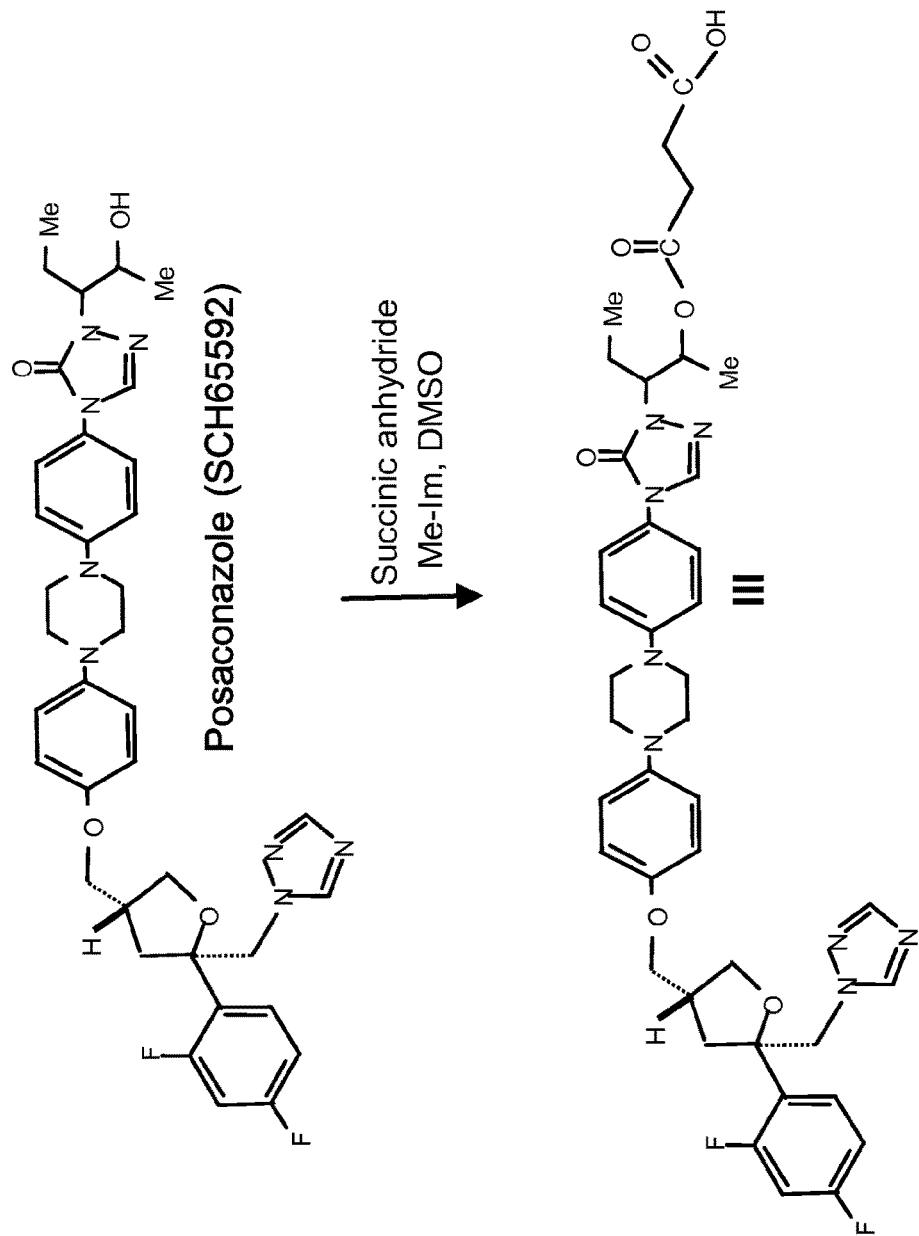
FIG. 3 illustrates the derivatization of poscanazole with 7-aminoDDAO.
Figure 3:
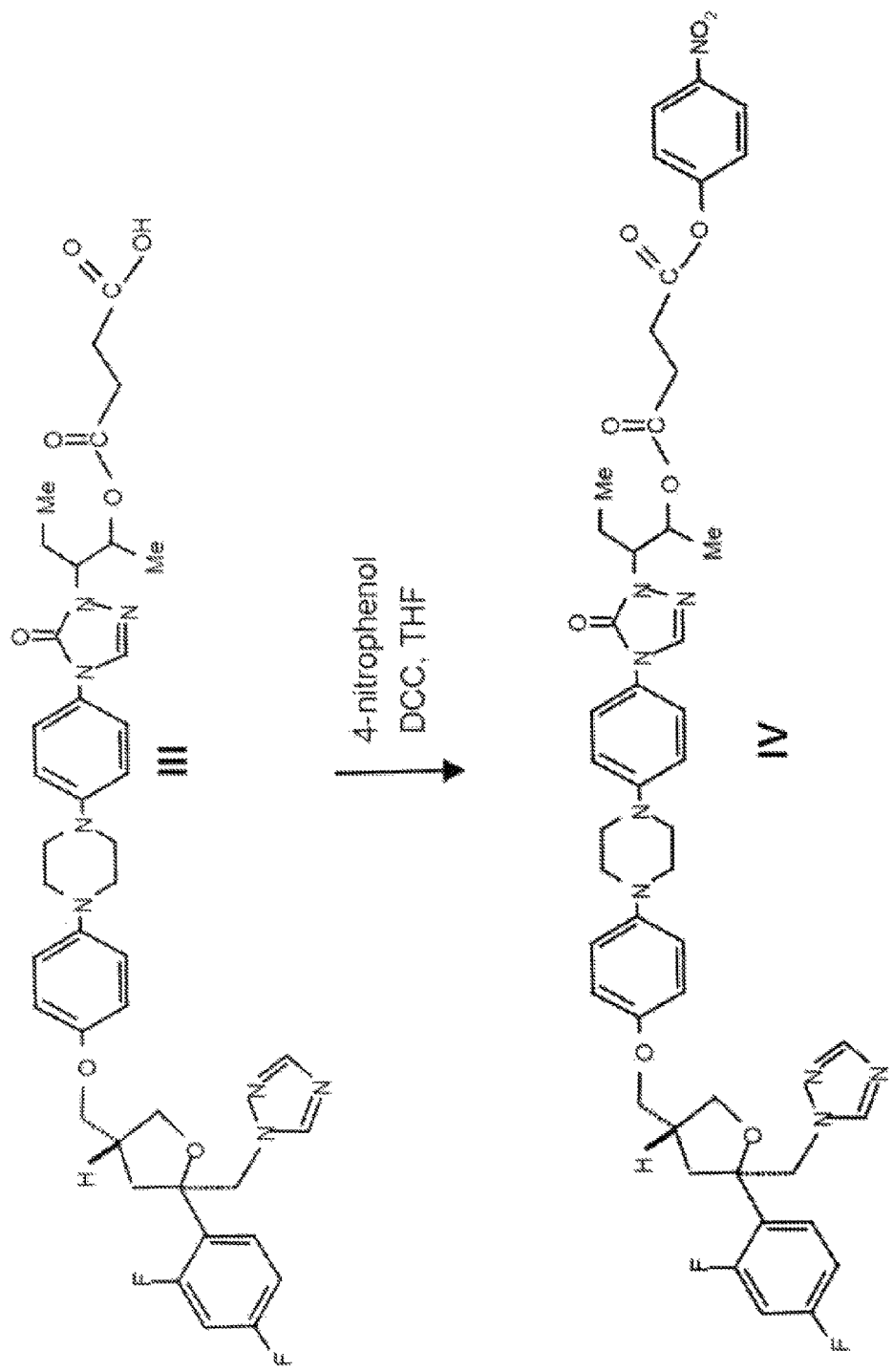
Figure 3:
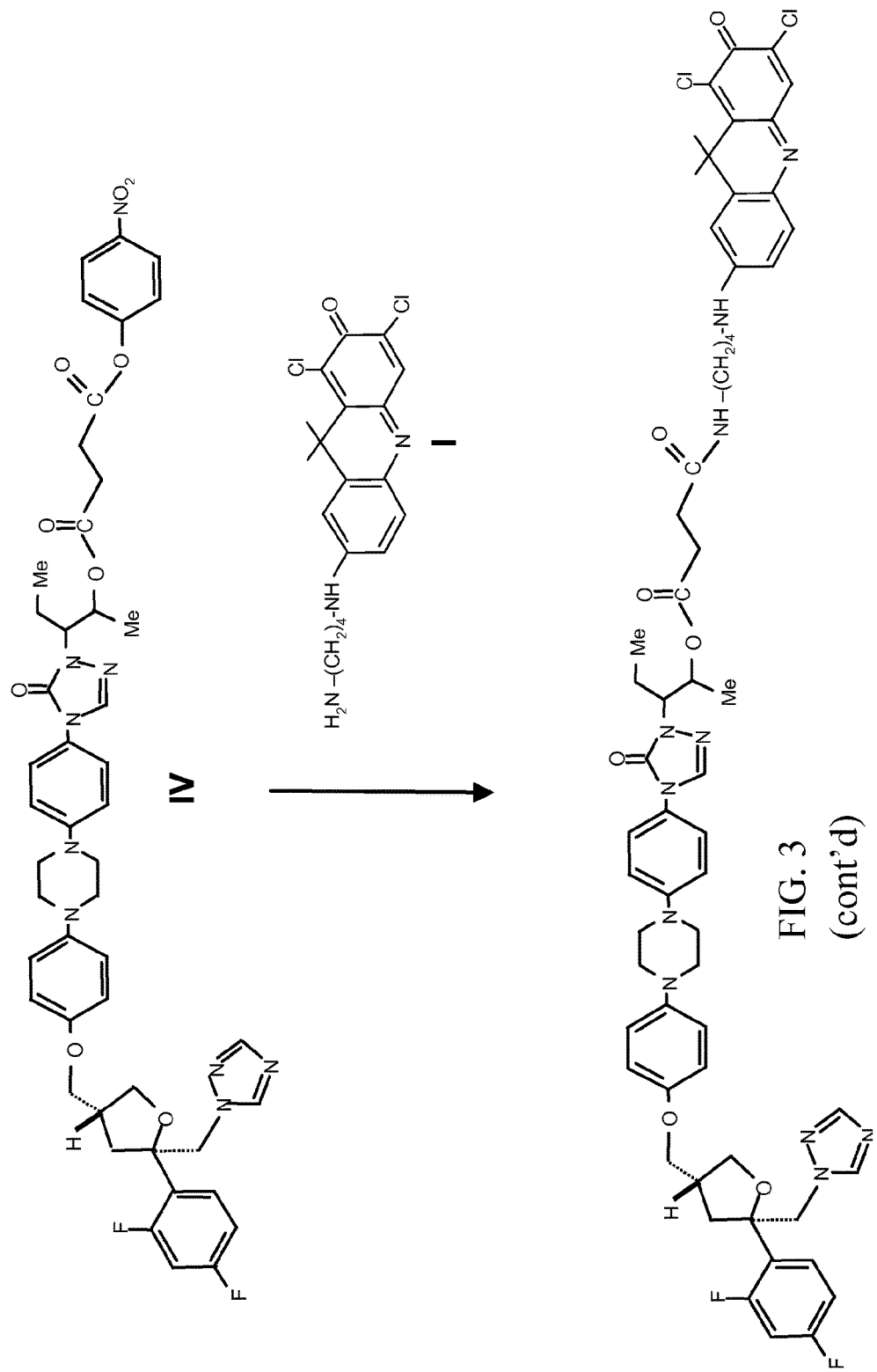

Compound III (FIG. 3)

A solution of 38 mg of posaconazole in 0.3 ml of DMSO was supplemented with 70 mg of succinic anhydride and 60 ml of methylimidazole. After 5 h incubation at 45° C. TLC analysis in chloroform-ethanol-20% ammonium hydroxide (100:10:1) revealed ca. 95% conversion of posaconazole to acylation product. The mixture was poured dropwise into 3 ml of 1 M citric acid and left for 30 min at 4° C. The precipitate was collected by centrifugation, washed with water (4×3 ml) and dried in vacuo under gentle heating. Yield: 30 mg. High resolution MS (MALDI) m/z: anal. calc. for $C_{41}H_{46}N_8O_7F_2$ 800.87; found 799.3.

Example 7

Compound IV (FIG. 3)

To a solution of 30 mg of Compound I in 0.3 ml of THF were added 10 mg of 4-nitrophenol and 25 mg of DCC. After 30 min incubation at 20° C. TLC analysis in a chloroform-ethanol (3:1) developing system revealed nearly quantitative conversion of compound III to reaction product. The precipitate was removed by centrifugation, and the reaction mixture to evaporated to dryness under reduced pressure. High resolution MS (MALDI) m/z: anal. calc. for $C_{47}H_{49}N_9O_9F_2$ 921.97; found 923.4.

Example 8

Posaconazole-DDAO Derivative

Two milligrams of compound IV of FIG. 2 were dissolved in 0.1 ml of 20 mM solution of compound I of FIG. 1. The mixture was supplemented with 2 µl of triethylamine and left for 20 min at room temperature. TLC analysis in ethylacetate-ethanol (8:1) developing mixture revealed complete conversion of compound I to reaction product. The mixture was diluted by 2 ml of water, and the residue was collected by centrifugation, dissolved in DMF and subjected to preparative TLC in the same system. Yield: 0.5 µmol.

Example 9

Derivatization of Core DDAO Compounds

To derivatize core DDAO compound Hamilton reaction previously discovered with simpler phenol-, or naphtol-derivatives was used (Malmberg, E., W., Hamilton, C., S., *J. Am. Chem. Soc.* 70, 2415, (1948); Willenz, J. *J. Chem. Soc.,* 1955, 2049). The reaction included acid-catalyzed attack of amino-compounds on mesomeric keto-form of the aromatic hydroxy-derivatives. The reaction product with 1,4-diaminobutane (FIG. 1) was obtained with high yield and purified by extraction. The resulting DDAO amino-derivative was converted to corresponding isothiocyanate (ITC) (compound III) by treatment with thiocarbonyldiimidazole followed by incubation with trifluoroacetic acid (FIG. 1). Thiol-reactive DDAO derivatives (compounds IV and V) were obtained by treatment of compound II with 4-nitrophenylbromoacetate, or succinimide ester of 3-maleimidopropionic acid respectively. Obtained 7-aminoDDAO derivative III was used to label antifungal drugs posaconazole and caspofungin (FIG. 2). Caspofungin was derivatized by the ITC in single-step reaction as one of the drugs two aliphatic amino groups. To introduce DDAO fluorescent label in posaconazole molecule the drug was first acylated at hydroxyl group by succinic anhydride in DMSO in the presence of nucleophilic catalyst, N-methylimidazole (FIG. 3). The resulting product was converted to an activated ester by incubation with 4-nitrophenole and DCC. This synthetic intermediate was introduced in reaction with 1,4-diaminobutyl-DDAO compound to yield the final product, which was purified using preparative TLC.

Example 10

Figure 4:
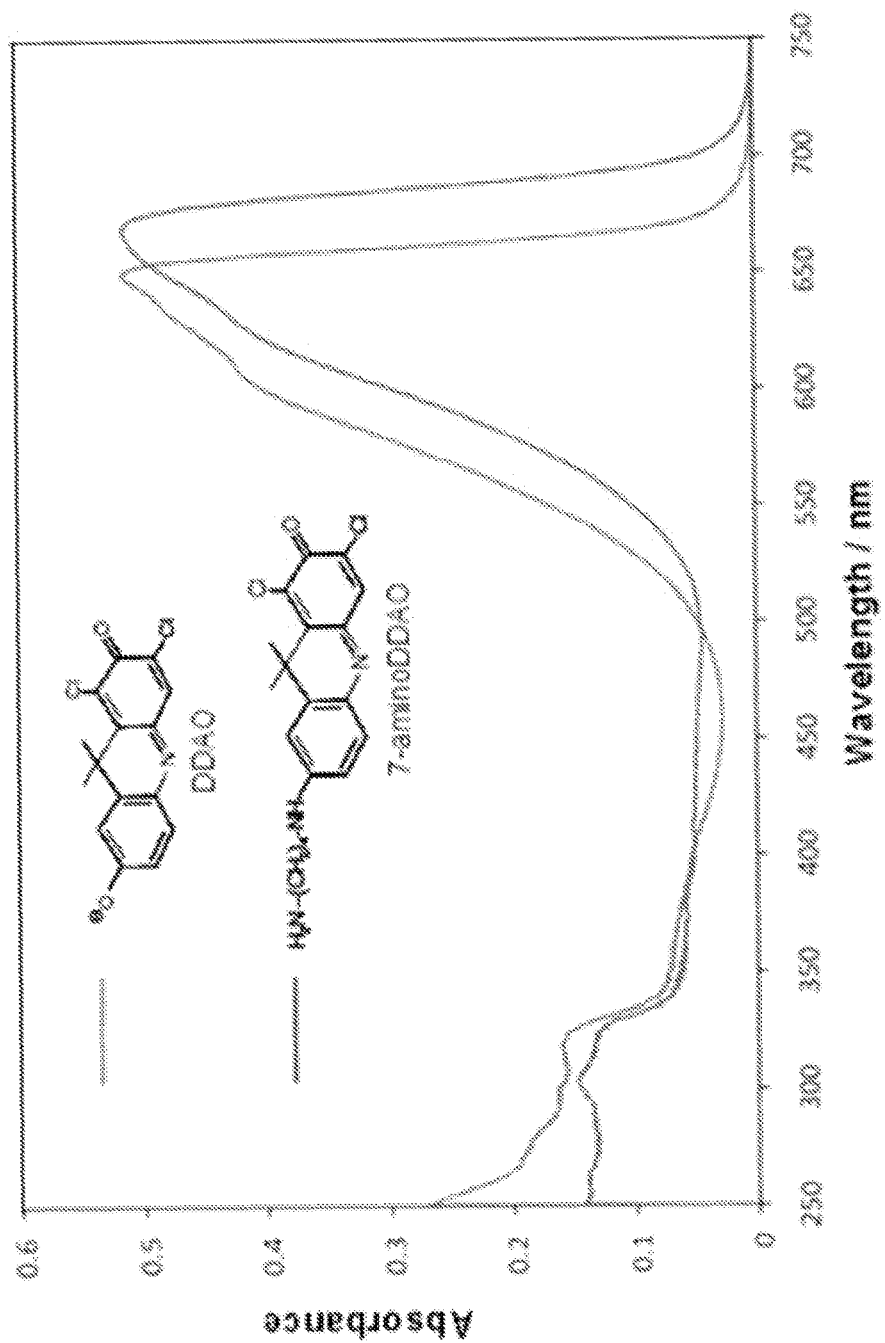
FIG. 4 depicts the light absorption spectra of DDAO and 7-aminoDDAO derivatives in 50% MeOH.

Light Absorption and Fluorescent Spectra of 7-aminoDDAO, caspofungin-DDAO, and posaconazole-DDAO Derivatives Modification of DDAO (FIG. 4) resulted in detectable blue shift of the light absorption maximum (653 nm and 673 nm correspondingly). The molar extinction of 7-aminoDDAO (55 000 M-1 cm-1) was determined by the attachment of reference chromophores with known molar absorptivity (Table 1). Light absorption spectra of the labeled caspofungin and posaconazole derivatives were close to superposition of those for the 7-(4-aminobutyl)amino-DDAO and the corresponding drugs, which is illustrated in FIG. 4 on the example of posaconazole derivative. The fluorescence spectra (FIG. 5B) of 7-(4-aminobutyl)amino-DDAO exhibited blue shift compared to ionized form of DDAO (FIG. 5A). Thus, excitation and emission maxima for DDAO were 653 nm and 660 nm correspondingly, while for 7-(4-aminobutyl)amino-DDAO they shifted to 671 nm and 679 nm correspondingly. This beneficial spectral shift brings the emission maximum in the region where the body tissues are the most transparent, see FIG. 6, which shows light absorption spectrum of body tissue and emission properties of reporter DDAO fluorophore. 7-Amino DDAO is chemically and photochemically stable, and thus reduces photo bleaching. Increasing content of the organic solvent (MeOH) resulted in enhancement of the light emission and characteristic change in excitation spectrum. Thus substitution 50% methanol for water did not affect the shape of the excitation spectrum for 7-aminoDDAP, but increased the light emission ca. 2.5 fold. Placing the compound in 100% MeOH resulted in dramatic change of the excitation spectrum profile shifting the maximum from 670 nm to 620 nm, while only slightly shifting emission maximum from 680 to 670 nm. Notably, the light emission intensity dropped 1.7 fold. Remarkably, the shape of the excitation spectrum curve for ionized form of DDAO was the same in 50% and 100% methanol. Also, in contrast to 7-aminoDDAO 1.3 fold increase in the emission was observed in 100% methanol compared to 50% methanol.

Figures 5C, 5D:
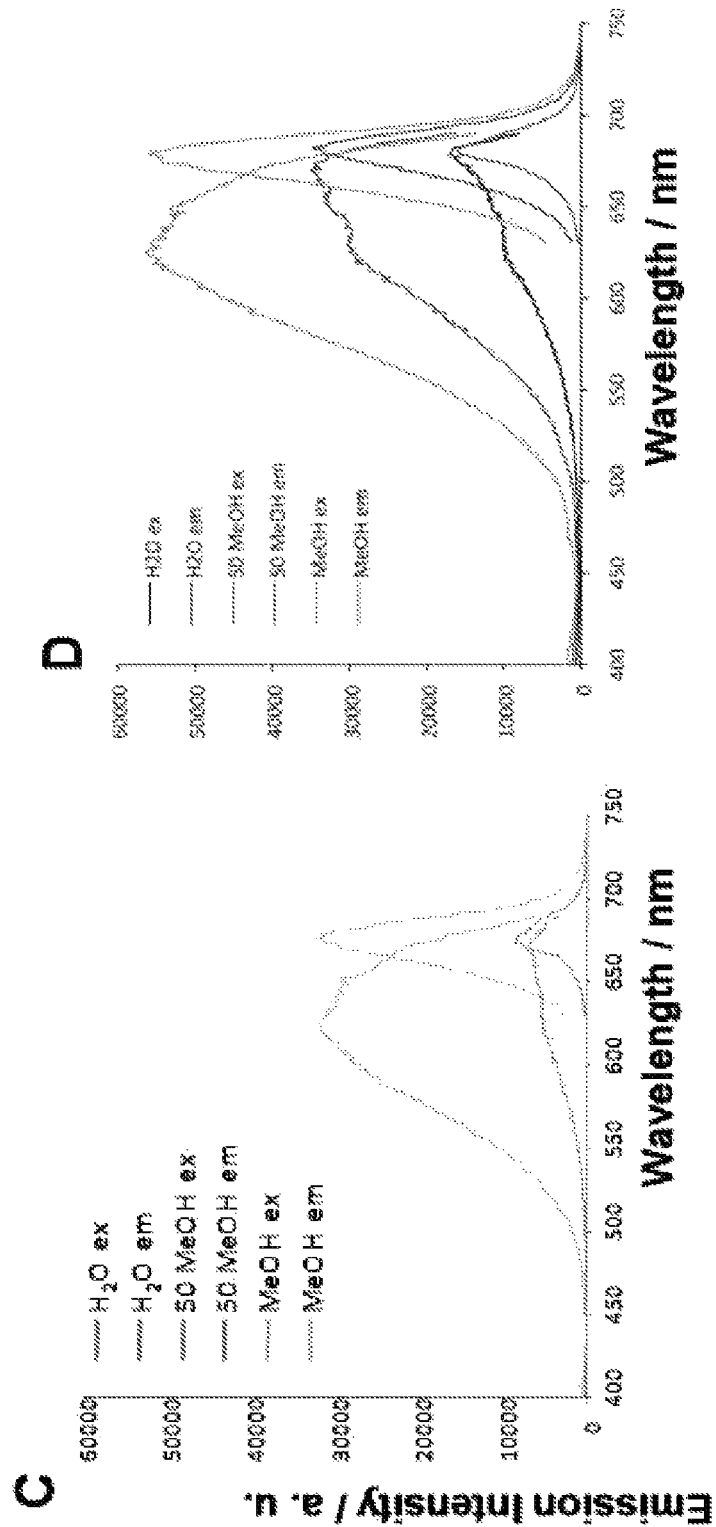
FIG. 5 depicts fluorescence spectra for DDAO at pH 9.0 (A), 7-aminoDDAO (B), 7-aminoDDAO-Pos (C), and 7-aminoDDAO-Casp (D) in various solvents.
Figure 6A:
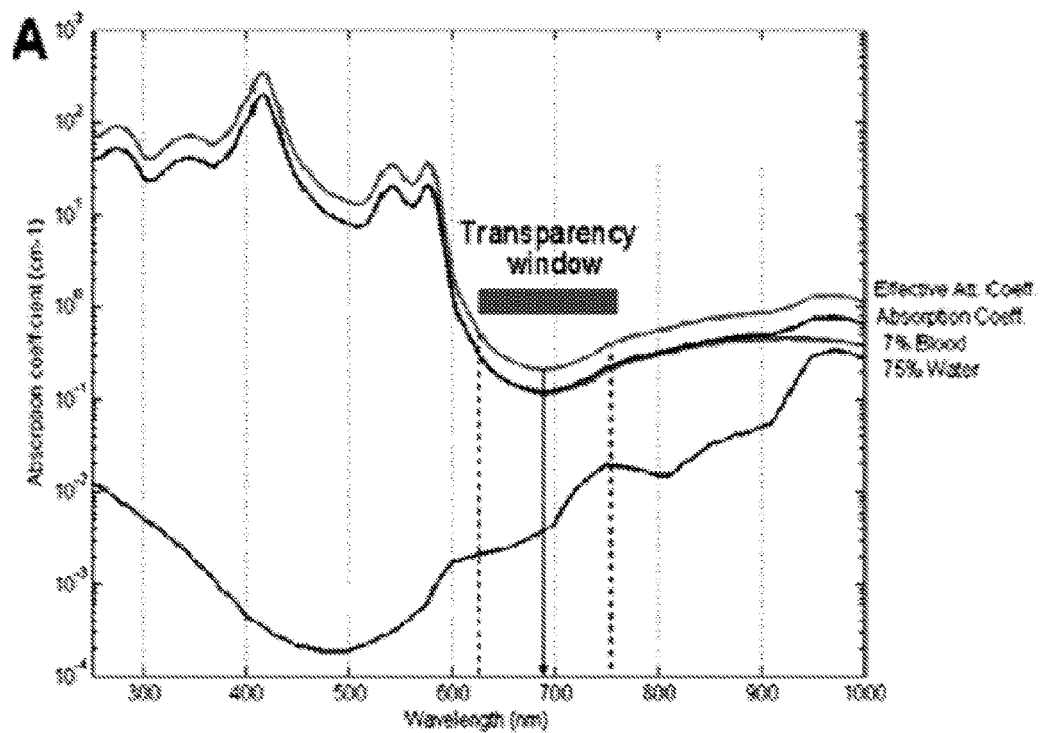
FIG. 6 depicts light transparency window for body tissues and the near infrared emission of 7-aminoDDAO.
Figure 6B:
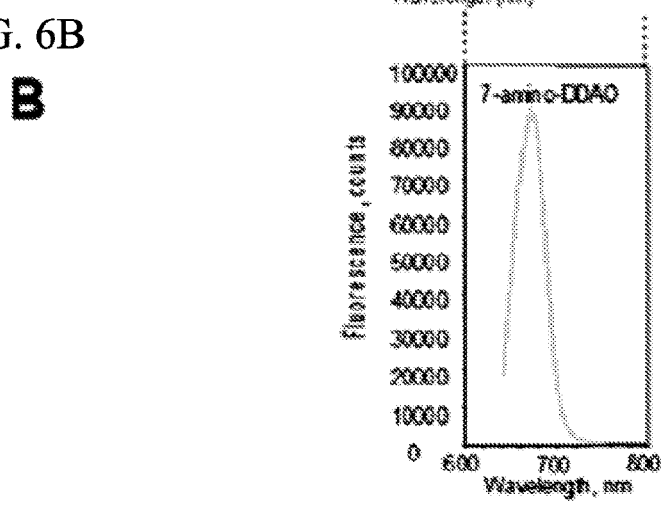
Figure 7:
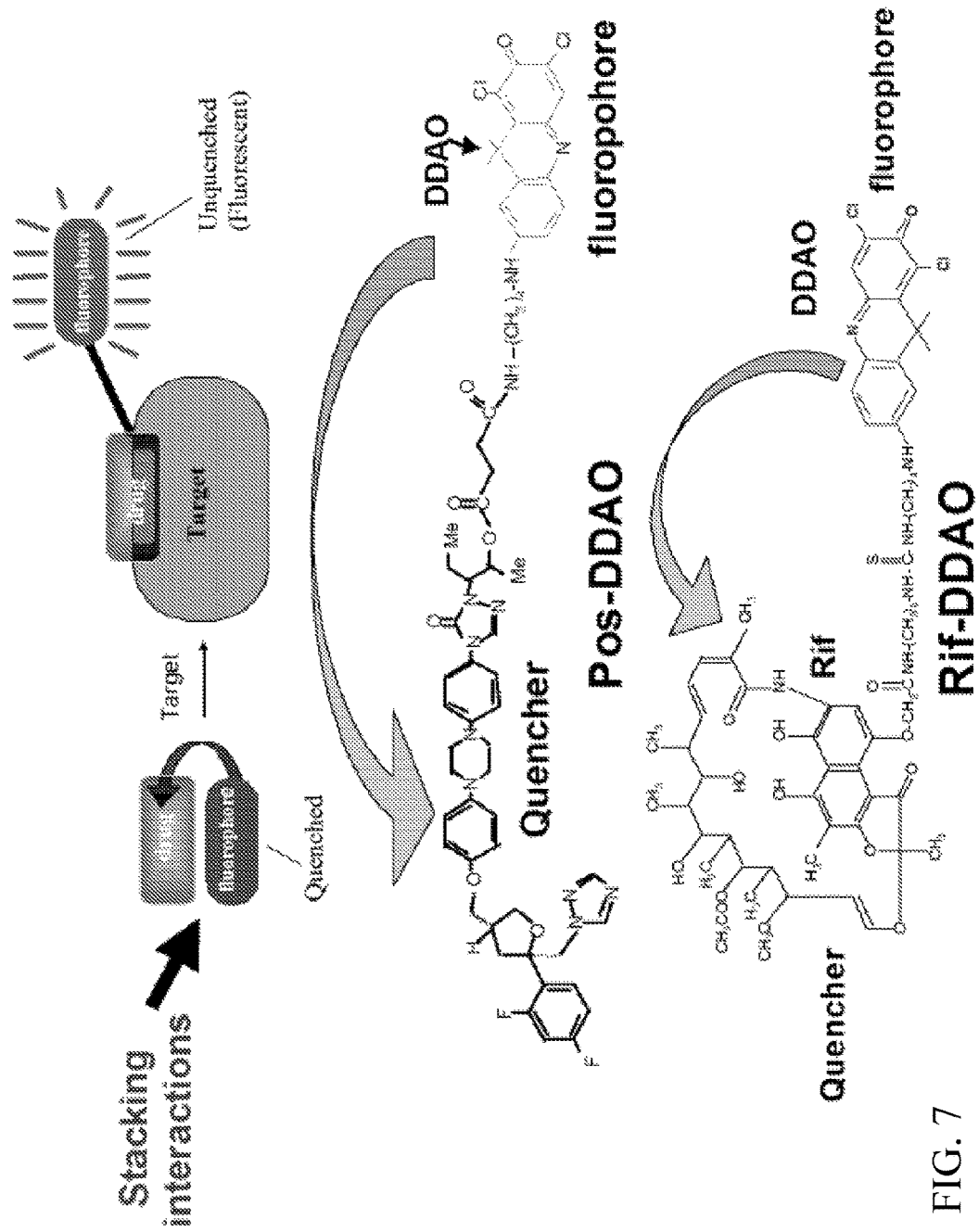
FIG. 7 illustrates the light emission properties of Posconazole-7-aminoDDAO and Rifampicin-7-aminoDDAO derivatives.

Similar trends in fluorescence spectra were observed for the 7-aminoDDAO fluorophore attached to caspofungin. As seen from FIG. 5D for the labeled drug the emission in 50% methanol increased 2 fold compared to the emission in water, however contrary to the free 7-aminoDDAO dye in 100% methanol further 1.3 fold increase was observed for caspofungin derivative emission. However, posaconazole derivative behaved differently. Thus in water the emission was completely quenched (FIG. 5C). The presence of 50% methanol in the medium greatly increased the emission, which was further (ca. 3 fold) enhanced in 100% methanol. The suppression of the fluorophore light emission in posaconazole derivative is likely due to the presence of extended light-absorbing moiety that can stack to the fluorophore, causing contact quenching (FIG. 7). The same change in fluorescence is expected upon interaction of the labeled drug with its cellular target, whereby stacking interactions of the fluorophore with the drug moiety have to be destroyed (FIG. 7B). This beneficial "signaling" effect is expected to greatly increase the contrast of imaging by minimizing the background signal of non-bound compound, which remains "dark".

TABLE 1

Molar absorption of 7-(4-aminobutyl)aminoDDAO calculated by using various chromophores attached to the aliphatic amino group.

| Attached compound | Molar absorption for attached compounds ($\epsilon/M^{-1}cm^{-1}$) | Calculated molar absorption for DDAO residue ($\epsilon/M^{-1}cm^{-1}$) |
| --- | --- | --- |
| Posaconazole | 34,000 | 59,000 |
| DNP | 17,600 | 32,000 |
| BODIPY-FL | 82,000 | 70,000 |
|  | Average | 53,000 |

TABLE 2

Relative Brightness (RB) and quantum yield (QY) in 3 different solvents for DDAO and its derivatives at [1 µM].

| Compounds | $\epsilon/M^{-1}cm^{-1}$ | RB ($H_2O$) | RB (50% MeOH) | RB (MeOH) | QY ($H_2O$) | QY (50% MeOH) | QY (MeOH) |
| --- | --- | --- | --- | --- | --- | --- | --- |
| DDAO (pH 9.0) | 48,000 | 6,000 | 9,000 | 12,000 | 0.125 | 0.19 | 0.25 |
| DDAO $NH_2$ | 53,000 | 10,000 | 21,000 | 13,000 | 0.19 | 0.40 | 0.25 |

TABLE 2-continued

Relative Brightness (RB) and quantum yield (QY) in 3 different solvents for DDAO and its derivatives at [1 μM].

| Compounds | ε/M⁻¹cm⁻¹ | RB (H₂O) | RB (50% MeOH) | RB (MeOH) | QY (H₂O) | QY (50% MeOH) | QY (MeOH) |
|---|---|---|---|---|---|---|---|
| DDAO Pos | 53,000 | 0.0 | 3,300 | 13,000 | 0.0 | 0.16 | 0.24 |
| DDAO Casp | 53,000 | 6,000 | 13,800 | 22,000 | 0.11 | 0.26 | 0.42 |
| Cy 5.5 (Ref) | 250,000 | 57,500 | N/A | N/A | 0.23 | NA | NA |

Table 2 illustrates light emission properties of DDAO-based diagnostic probes and reference compounds, and presents the data on quantum yield and brightness for 7-aminoDDAO compound at various conditions. These parameters were determined using a reference fluorophore Cy5.5, (which has the excitation and emission maxima nearly identical to those for 7-aminoDDAO) and published data for original DDAO fluorophore. It is seen that synthesized 7-aminoDDAO derivative possessed higher brightness (Ø=10 000) compared to ionized original DDAO compound (Ø=6 000). This was perhaps due to higher light absorptivity and higher quantum yield of the amino-derivative. The difference in brightness further increased in 50% methanol (21 000 and 9000 correspondingly). However, in 100% methanol the brightness became comparable (13 000 and 12 000 correspondingly).

Example 11

Use of Caspofungin-DDAO Derivative for Imaging of Fungal Infections in Mice

Figure 8A:
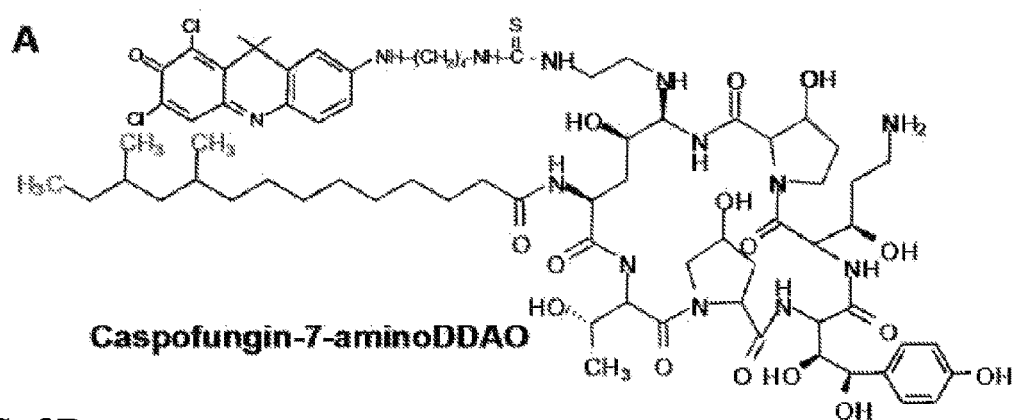
FIG. 8 depicts the use of 7-aminoDDAO labeled casponfungin for imaging of infected mice kidneys.
Figure 8B:
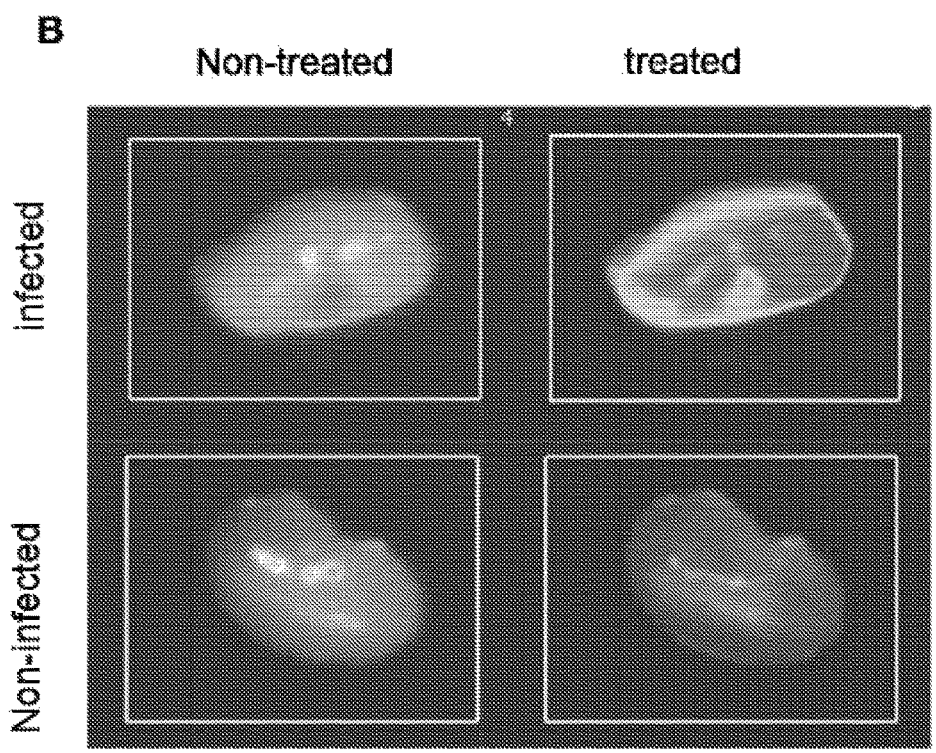

FIG. 8 shows the results on imaging of mice kidney infected with a fungal pathogen along with control images. Mice were infected via intravenous inoculation with 5*10⁵ CFU of wild type *Candida albicans* and an infection that occurs most prominently in the kidneys. After 48 hours post infection, a fixed concentration of 0.12 ug/mL of CSF-DDAO is added via tail vein injection at 0, 2, 4 and 8 hours to assess the optimal time for visualization of the infection. At each time point, the mice were imaged in a non-invasive whole-body animal imaging system to detect fluorescence energy. Animals infected with *Candida albicans* show proliferation of the fungal infection in the kidneys after 48 hours. The addition of CSF probe resulted in progressive labeling of cells in the target organs over time, as determined by whole body imaging. Maximum labeling occurred at 8 hours. CSF-DDAO did not accumulate in the kidneys in the absence of infection. It is seen that treatment of the infected organ with caspofungin-7-aminoDDAO derivative resulted in bright fluorescent signal. At the same time no signal was detected in uninfected and/or untreated organs.

Figure 9:
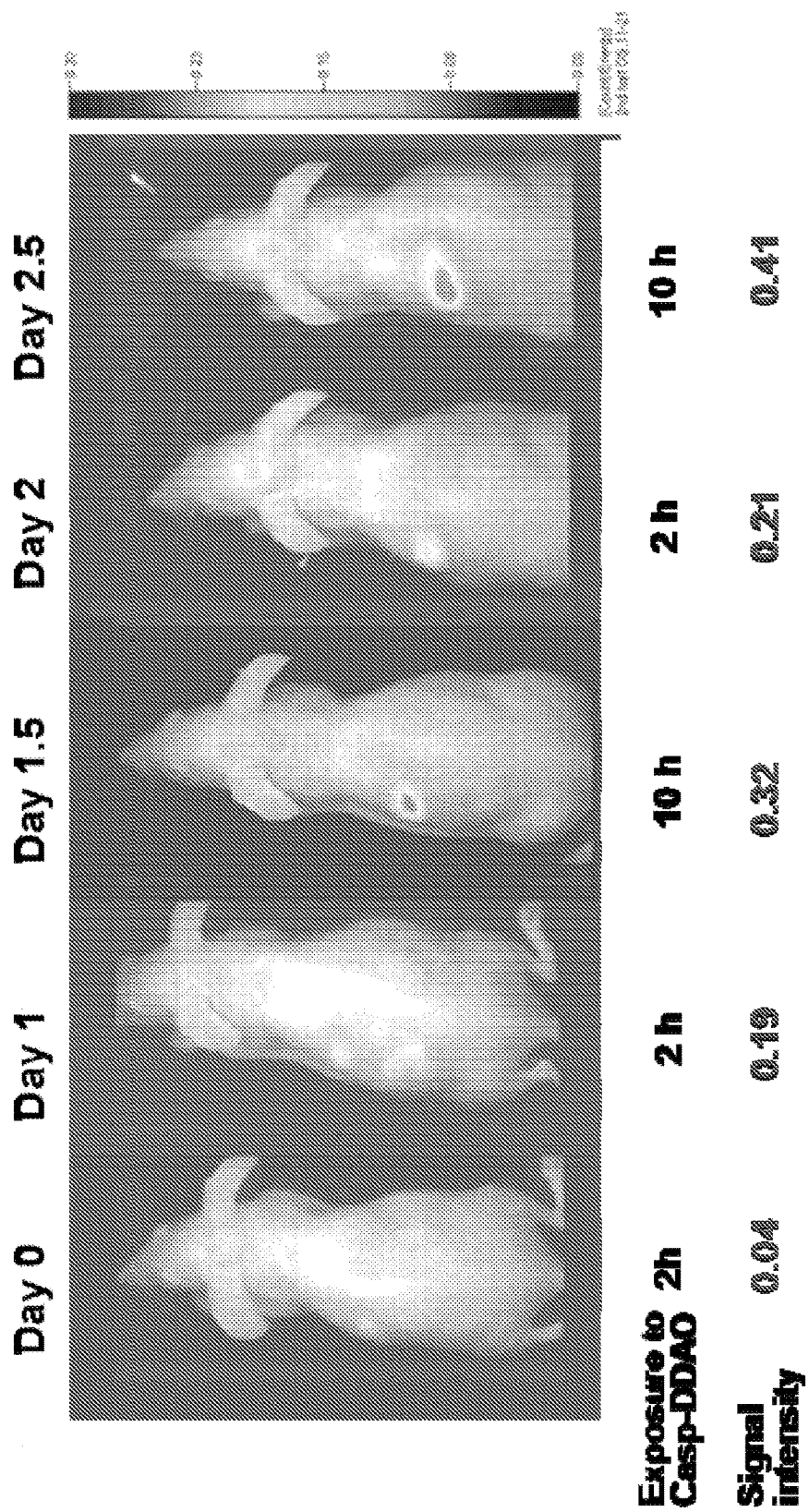
FIG. 9 depicts tomographic detection of C. albicans in live mice using fluorescent Casp-DDAO compound.

The tomographic detection of *C. albicans* in live mice using fluorescent CSF-DDAO compound is shown in FIG. 9. Mice were infected and treated with caspofungin-containing diagnostic probe essentially as described in the previous section, followed by FMT imaging after indicated time elapsed from the infection event. The animals imaging was performed after 2 or 10 hours following the injection of the diagnostic probe. Peak signal intensity is presented for each scan.

Example 12

Synthesis of Rifampicin-DDAO Compound

Rifamycin B (0.1 mmol) in 0.5 ml of anhydrous THF was supplemented with 0.5 mmol of DCC and kept at room temperature for 30 min, followed by addition of 0.5 mmol of 1,6-diaminohexane. After 10 min incubation aminohexyl derivative of Rif was purified by TLC in a chloroform/ethanol developing system (2:1). The product was eluted by methanol and evaporated to dryness in vacuo Aminohexyl Rif derivative and NCS-DDAO compound III of FIG. 1 (1 mmol of each) were dissolved in 0.05 ml of DMF and mixed. After incubation at 60° C. for 1 h the Rid-DDAO adduct was purified by TLC in chloroform-ethanol developing system (3:1), eluted by methanol and evaporated to dryness under reduced pressure. The residue was dissolved in DMSO (0.2 ml) and kept at −80° C. Yield: 40%.

Example 13

Determination of Minimal Inhibitory Concentration (MIC) for Rif-DDAO Compound with *B. subtilis* and *S. aureus*

Figure 10:
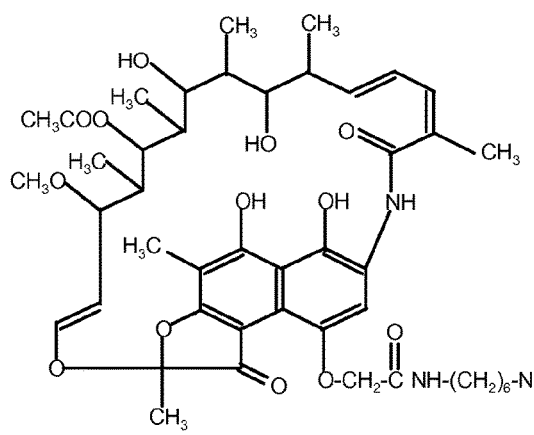
FIG. 10 illustrates synthesis and validation of light-emitting probes for diagnostic imaging of microbial infections.
Figure 10:
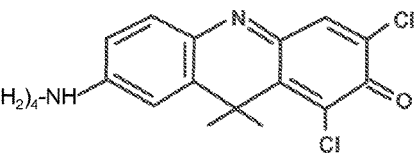
Figure 10:
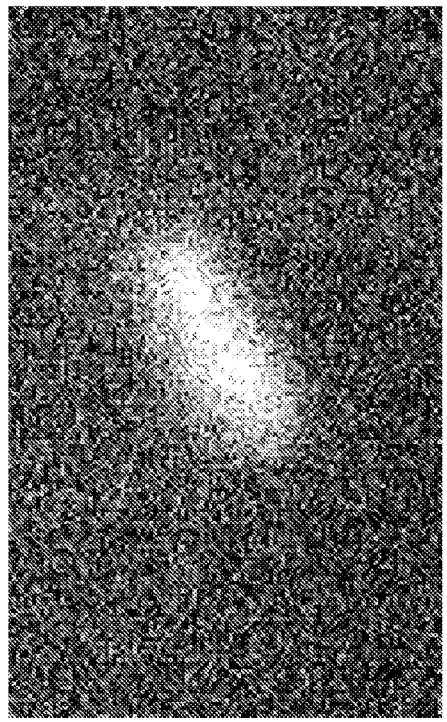
Figure 10:
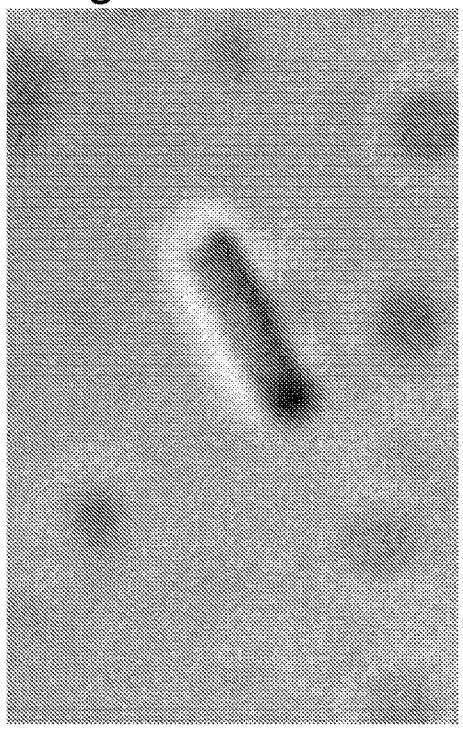

This was performed by using serial dilution method in 96-well plates with starting concentration of bacteria 10⁵ CFU/ml. The bacterial growth was inspected visually after 12 h incubation at 37° C. The results are shown in FIG. 10.

Example 14

Imaging of Cultured *B. subtilis* Cells Using Rif-DDAO Derivative

Bacteria were grown to the density ~0.2 a.u./ml followed by addition of Rif-DDAO compound to final concentration 0.5 μM. After incubation for 30 min the cells were collected by centrifugation and imaged using fluorescent microscopy. The results are presented in FIG. 10.

The synthesized DDAO derivatives, in particular 7-aminoDDAO derivatives, are excellent candidates for bioimaging. This has been successfully demonstrated by visualization of a fungal pathogen in mice kidney. Beneficial spectral properties of the fluorophore combined with its small size make it useful in design of various diagnostic affinity probes in cellular studies as well as in biomedical applications.

The foregoing description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and are intended to be included within the scope of the following claims.

What is claimed is:

1. A compound of formula (I):

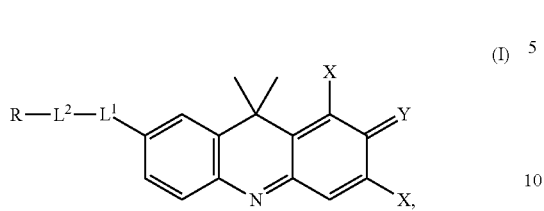

or a pharmaceutically acceptable salt or solvate thereof, wherein:

X at each occurrence is independently a halogen;

Y is O, S, or $NR^y$, wherein $R^y$ is hydrogen or $C_1$-$C_4$ alkyl;

$L^1$ is —NH—;

$L^2$ is a bond, a linear or branched alkylene, or a linear or branched heteroalkylene; and R is hydrogen, a moiety of a biologically active molecule, or a functional group that can react with a biologically active molecule to form a covalent bond.

2. The compound of claim 1, wherein said alkylene has from 1 to 20 carbon atoms, and said heteroalkylene has from 1 to 15 carbon atoms and from 1 to 5 heteroatoms independently selected from O, N and S.

3. The compound of claim 1, wherein $L^2$ is —$(CH_2)_m$— or —$(CH_2CH_2O)_a$—$(CH_2)_b$—, wherein m is an integer selected from 1 to 10; a is 0 or an integer selected from 1 to 5, and b is an integer selected from 1 to 4.

4. The compound of claim 1, wherein:

R is —$NR^aR^b$, —NCS, —NCO, $C_1$-$C_6$ alkyl, amido, substituted or unsubstituted maleimido, a click-reactive group, or —C(O)—$R^1$;

wherein $R^a$ and $R^b$ are independently hydrogen or $C_1$-$C_4$ alkyl;

$R^1$ is —$N_3$ or —$OR^2$; and $R^2$ is $C_1$-$C_6$ alkyl or succinimido.

5. The compound of claim 4, wherein said click-reactive group is —$N_3$ or —C≡CH.

6. The compound of claim 1, wherein R is a moiety of a biologically active molecule.

7. The compound of claim 6, wherein said biologically active molecule is small molecule selected from the group consisting of antibacterial and antifungal agents.

8. The compound of claim 6, wherein said biologically active molecule is a large molecule selected from the group consisting of an antibody, an antigen, a carbohydrate, a peptide, a nucleic acid, a lipid, and a synthetic or natural polymer.

9. The compound of claim 1, wherein $L^1$ is —NH—; and $L^2$ is —$CH_2CH_2CH_2CH_2$—.

10. The compound of claim 1, wherein both X are Cl, and Y is O.

11. The compound of claim 1, selected from the group consisting of 7-amino-9H-(1,3-dichloro-9,9-dimethylacridin-2-one)(7-aminoDDAO), DDAO-NH—$(CH_2)_4$—$NH_2$, DDAO-NH—$(CH_2)_4$—NCS, DDAO-NH—$(CH_2)_4$—NH—$COCH_2X$ (wherein X is halogen), DDAO-NH—$(CH_2)_4$—NH-3-maleimide, and a conjugate between Rifampicin and 7-aminoDDAO.

12. The compound of claim 1, having a formula (II):

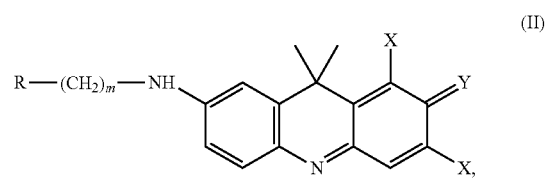

wherein R is selected from the group consisting of:

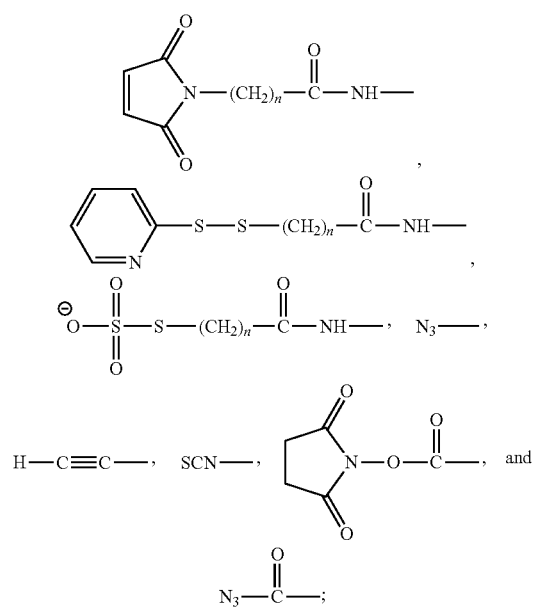

each X is independently a halogen;

Y is O, S, or $NR^y$, wherein $R^y$ is hydrogen or $C_1$-$C_4$ alkyl;

m is an integer selected from 1 to 10; and n at each occurrence is independently an integer selected from 1 to 10.

13. The compound of claim 12, wherein each X is independently F, Cl, or Br; m is 2 to 6; and n at each occurrence is 1 to 6.

14. The compound of claim 12, wherein X is Cl; Y is O; m is 2 to 4; and n at each occurrence is 2 to 4.

15. A method of detecting a cell or a target in a cell of or detecting a microbe in, a subject, comprising administering to the subject a compound of claim 1, exciting said compound with photons comprising NIR wavelength photons and detecting NIR fluorescence of the compound.

16. A method of detecting a cell or a target in a cell of a biological sample, comprising contacting the biological sample with a compound of claim 1, exciting said compound with photons comprising NIR wavelength photons and detecting NIR fluorescence of the compound.

17. A bioconjugate comprising a targeting agent, a moiety of a 7-aminoDDAO, and a linking group through which said 7-aminoDDAO is coupled to said targeting agent, wherein the targeting agent is an agent capable of detecting a target of interest in a biological sample or a subject.

18. The bioconjugate of claim 17, wherein the targeting agent is an antibody, an antigen, a carbohydrate, a peptide, a nucleic acid, a lipid, a synthetic or natural polymer, a small molecule, or a combination thereof.

19. The bioconjugate of claim 17, wherein the target of said targeting agent is a glycoprotein, lipopolysaccharide, lipopeptide, a component of a cell wall, a receptor, or a combination thereof.

20. The bioconjugate of claim 17, wherein the linking group is selected from the group consisting of peptide linkers, self-immolative linkers, acid sensitive linkers, multifunctional organic linking agents, bifunctional inorganic crosslinking agents, polymers, and combinations thereof.

21. A method of detecting a cell or a target in a cell of, or detecting a microbe in a subject, comprising administering to the subject a bioconjugate of claim 17, exciting said bioconjugate with photons comprising NIR wavelength photons and detecting NIR fluorescence of the bioconjugate.

* * * * *

UNITED STATES PATENT AND TRADEMARK OFFICE
CERTIFICATE OF CORRECTION

PATENT NO. : 9,700,638 B2
APPLICATION NO. : 14/889215
DATED : July 11, 2017
INVENTOR(S) : Mustaev et al.

Page 1 of 1

It is certified that error appears in the above-identified patent and that said Letters Patent is hereby corrected as shown below:

In the Specification

At Column 1, Line number 20, reads:
"The invention described herein was supported in whole or in part by grants from the National Institutes of Health (NIH-GM-30717-21). The U.S. Government has certain rights in this invention."
Should read:
--This invention was made with government support under grant number GM030717 awarded by the National Institutes of Health. The government has certain rights in the invention.--

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*